(12) United States Patent
Kakuyama et al.

(10) Patent No.: US 11,517,751 B2
(45) Date of Patent: Dec. 6, 2022

(54) ELECTRODE FOR ELECTRICAL STIMULATION THERAPY AND ELECTRICAL STIMULATION THERAPEUTIC DEVICE

(71) Applicants: OTSUKA TECHNO CORPORATION, Naruto (JP); ITO CO., LTD., Tokyo (JP)

(72) Inventors: Hiroki Kakuyama, Naruto (JP); Tetsuya Masuda, Naruto (JP); Makoto Sasaki, Tokyo (JP)

(73) Assignees: OTSUKA TECHNO CORPORATION, Naruto (JP); ITO CO., LTD., Tokyo (JP)

( * ) Notice: Subject to any disclaimer, the term of this patent is extended or adjusted under 35 U.S.C. 154(b) by 0 days.

(21) Appl. No.: 17/254,475

(22) PCT Filed: Dec. 26, 2019

(86) PCT No.: PCT/JP2019/051117
§ 371 (c)(1),
(2) Date: Dec. 21, 2020

(87) PCT Pub. No.: WO2020/183868
PCT Pub. Date: Sep. 17, 2020

(65) Prior Publication Data
US 2021/0113833 A1 Apr. 22, 2021

(30) Foreign Application Priority Data
Mar. 8, 2019 (JP) .............................. JP2019-042976

(51) Int. Cl.
*A61N 1/36* (2006.01)
*A61N 1/04* (2006.01)

(52) U.S. Cl.
CPC ....... *A61N 1/36007* (2013.01); *A61N 1/0492* (2013.01)

(58) Field of Classification Search
CPC .......................... A61N 1/36007; A61N 1/0492
(Continued)

(56) References Cited

U.S. PATENT DOCUMENTS

| 5,191,886 A | 3/1993 | Paeth et al. |
| 5,341,806 A | 8/1994 | Gadsby et al. |

(Continued)

FOREIGN PATENT DOCUMENTS

| EP | 2 050 480 A1 | 4/2009 |
| JP | 4-17163 Y2 | 4/1992 |

(Continued)

OTHER PUBLICATIONS

International Search Report, issued in PCT/JP2019/051117, dated Feb. 4, 2020.
(Continued)

*Primary Examiner* — Nadia A Mahmood
(74) *Attorney, Agent, or Firm* — Birch, Stewart, Kolasch & Birch, LLP

(57) ABSTRACT

An electrode for electrical stimulation therapy includes a sheet body of flat shape having a first surface facing a skin of a human body and a second surface at an opposite side to the first surface and at least one pair of flat electrodes that are provided at the first surface side of the sheet body and are mutually separated and the sheet body includes an expandable/contractible portion that is formed on a virtual axial line extending between the pair of flat electrodes and is expandable/contractible in a direction intersecting the virtual axial line. The electrical stimulation therapeutic device includes a device body and the electrode for electrical stimulation therapy electrically connected to the device body.

11 Claims, 28 Drawing Sheets

(58) Field of Classification Search
USPC .......................................................... 607/41
See application file for complete search history.

(56) References Cited

U.S. PATENT DOCUMENTS

| | | | |
|---|---|---|---|
| 10,035,016 B2* | 7/2018 | Kolb | .................. A61N 1/36014 |
| 2010/0318018 A1 | 12/2010 | Schonenberger et al. | |
| 2015/0290450 A1 | 10/2015 | Kolb et al. | |
| 2016/0184575 A1 | 6/2016 | Schonenberger et al. | |
| 2017/0182320 A1 | 6/2017 | Kolb et al. | |
| 2019/0105487 A1 | 4/2019 | Schonenberger et al. | |

FOREIGN PATENT DOCUMENTS

| | | |
|---|---|---|
| JP | 6-38938 A | 2/1994 |
| JP | 2008-36210 A | 2/2008 |
| JP | 4839457 B2 | 12/2011 |
| JP | 2012-24405 A | 2/2012 |
| WO | WO 2008/018359 A1 | 2/2008 |

OTHER PUBLICATIONS

Written Opinion of the International Searching Authority, issued in PCT/JP2019/051117, dated Feb. 4, 2020.

* cited by examiner

3

3

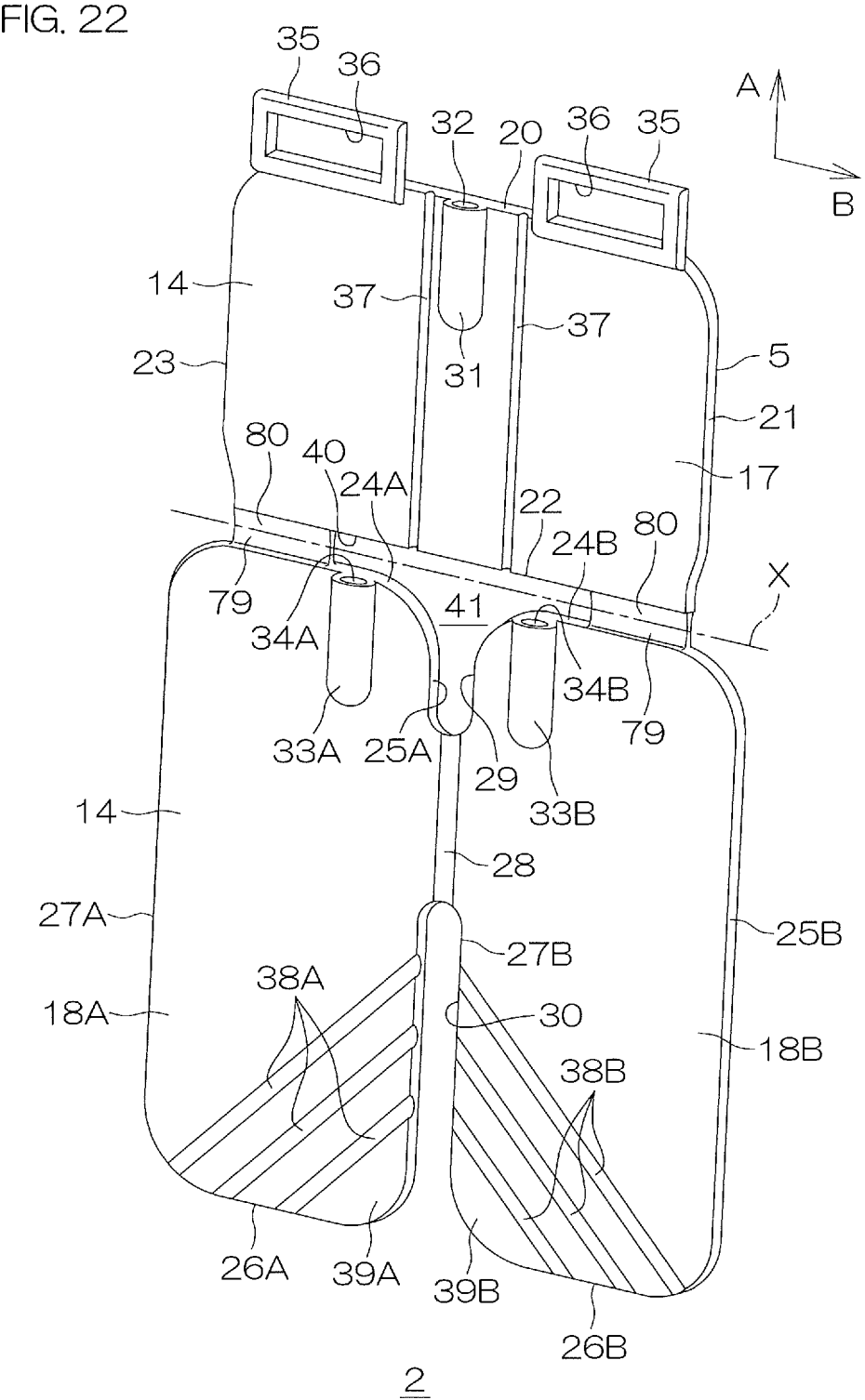

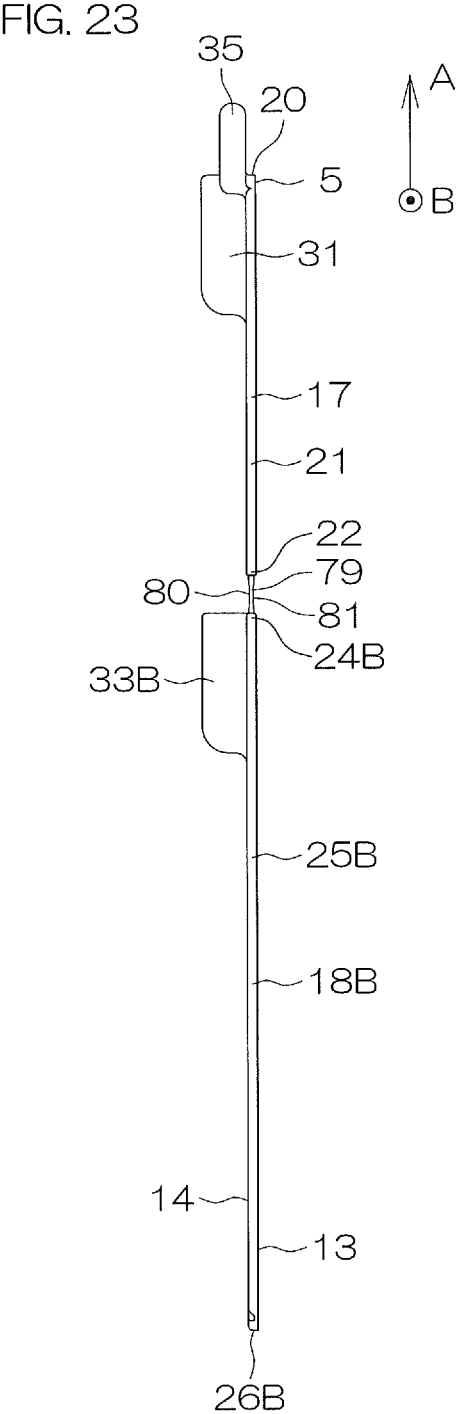

ELECTRODE FOR ELECTRICAL STIMULATION THERAPY AND ELECTRICAL STIMULATION THERAPEUTIC DEVICE

TECHNICAL FIELD

The present invention relates to an electrical stimulation therapeutic device used for electrical stimulation therapy and an electrode for electrical stimulation therapy included in the electrical stimulation therapeutic device.

BACKGROUND ART

For example, Patent Literature 1 discloses an electrode for electrical stimulation therapy that includes a sheet body of flat shape having flexibility, at least one pair of flat electrodes provided at one surface side of the sheet body and adherable to positions on a surface of the human body sandwiching a vertebral column, and a projection for positioning provided at the one surface side on the sheet body at which the flat electrodes are provided and being aligned, for example, to a coccyx, etc., that is a specific position of the human body.

CITATION LIST

Patent Literature

Patent Literature 1: Japanese Patent Application Publication No. 2012-24405

SUMMARY OF INVENTION

Technical Problem

If an electrode for electrical stimulation therapy such as the above is to be used upon being attached to a movable part of a human body, preferably, it is unlikely to become detached even when the human body moves.

Although if the electrode for electrical stimulation therapy includes one pair of mutually separated electrodes, it may be unlikely to become detached even when the human body moves, in this case, each electrode must be positioned individually and there is thus a problem of lack of ease of attachment.

An object of the present invention is to provide an electrode for electrical stimulation therapy that is unlikely to become detached even when a human body moves and an electrical simulation therapeutic device that includes the same.

Another object of the present invention is to provide an electrode for electrical stimulation therapy with which at least one pair of flat electrodes are easy to attach and an electrical simulation therapeutic device that includes the same.

Solution to Problem

An electrode for electrical stimulation therapy according to an embodiment of the present invention includes a sheet body of flat shape that has a first surface facing a skin of a human body and a second surface at an opposite side to the first surface and at least one pair of flat electrodes that are provided at the first surface side of the sheet body and are mutually separated and the sheet body includes an expandable/contractible portion that is formed on a virtual axial line extending between the one pair of flat electrodes and is freely expandable/contractible in a direction intersecting the virtual axial line.

According to this arrangement, the sheet body includes the expandable/contractible portion that is freely expandable/contractible. Thereby, if one flat electrode and the other flat electrode are attached, for example, across a flexing portion of the human body, application of an excessive force in a plane direction on the flat electrodes when the human body flexes (moves) can be suppressed by the expandable/contractible portion expanding or contracting in accordance with the flexing. Consequently, the flat electrodes can be made unlikely to become detached from the human body.

Also, since the at least one pair of flat electrodes are provided on the sheet body in common, by attaching at least one flat electrode at an appropriate position, positioning of the other flat electrode can be performed substantially automatically.

With the electrode for electrical stimulation therapy according to the embodiment of the present invention, the expandable/contractible portion may include an expandable/contractible portion that is formed along the virtual axial line and is bulgingly curved to the second surface side of the sheet body in a sectional view in the direction intersecting the virtual axial line.

With the electrode for electrical stimulation therapy according to the embodiment of the present invention, the expandable/contractible portion may be bulged in an arch shape to the second surface side of the sheet body in the sectional view when the sheet body is in a flat state.

According to this arrangement, the expandable/contractible portion expands/contracts smoothly and therefore, the application of an excessive force in a plane direction on the flat electrode can be suppressed further.

With the electrode for electrical stimulation therapy according to the embodiment of the present invention, the expandable/contractible portion of the arch shape may have a perimeter of 1 cm to 3 cm in the sectional view.

With the electrode for electrical stimulation therapy according to the embodiment of the present invention, the expandable/contractible portion may include an expandable/contractible portion that is of a folded line shape when the second surface of the sheet body is viewed from above and extends on a plane along the second surface of the sheet body.

With the electrode for electrical stimulation therapy according to the embodiment of the present invention, the expandable/contractible portion may include an expandable/contractible portion that is constituted of an elastic material and is flat along the second surface of the sheet body.

With the electrode for electrical stimulation therapy according to the embodiment of the present invention, the sheet body may include a first region at one side and a second region at another side that are opposed across the expandable/contractible portion in the direction intersecting the virtual axial line and the at least one pair of flat electrodes may include a first electrode disposed in the first region and a second electrode disposed in the second region.

With the electrode for electrical stimulation therapy according to the embodiment of the present invention, the first electrode may include one reference electrode and the second electrode may include one pair of stimulating electrodes.

With the electrode for electrical stimulation therapy according to the embodiment of the present invention, the expandable/contractible portion may include one pair of expandable/contractible portions that are mutually separated in a direction along the virtual axial line and an opening demarcated by the first region, the second region, and the one pair of expandable/contractible portions may be formed in the sheet body.

According to this arrangement, the positioning of the flat electrodes can be performed with a finger being hooked on the sheet body by passing the finger through the opening and the flat electrodes can thus be attached more easily. Also, when performing the positioning of the flat electrodes, by keeping the finger passed through the opening in contact with the human body, an appropriate attachment position for the electrode can be found easily by being guided by the finger passed through the opening. Further, a position of the sheet body can be finely adjusted with the finger passed through the opening as a support point and the positioning can thus be performed more easily.

The electrode for electrical stimulation therapy according to the embodiment of the present invention may further include a protruding portion formed in a periphery of at least one of the one pair of flat electrodes within the first surface of the sheet body.

According to this arrangement, the protruding portion is formed in the periphery of a flat electrode. Therefore, when, for example, an adhesive member such as a conductive adhesive pad, etc., is adhered on the flat electrode, the protruding portion is disposed at a periphery of the adhesive member. Consequently, even when the electrode for electrical stimulation therapy is moved during the positioning of the electrode for electrical stimulation therapy, the adhesive member can be held by the protruding portion and deviation of the adhesive member can be suppressed.

With the electrode for electrical stimulation therapy according to the embodiment of the present invention, a plurality of the protruding portions may be disposed at intervals from each other such as to surround the flat electrode.

According to this arrangement, the plurality of protruding portions are disposed at intervals from each other and therefore, the sheet body is easily bent in regions between mutually adjacent protruding portions and therefore, pliability of the sheet body can be secured.

An electrical stimulation therapeutic device according to an embodiment of the present invention includes a device body and the electrode for electrical stimulation therapy that is electrically connected to the device body.

According to this arrangement, since the electrode for electrical stimulation therapy of the present invention is included, the electrical stimulation therapeutic device with which the flat electrodes are unlikely to become detached even when the human body moves and with which the flat electrodes are easy to attach can be provided.

An electrical stimulation therapeutic device according to the embodiment of the present invention may include a device body, the electrode for electrical stimulation therapy, and a wiring member that connects the device body and the electrode for electrical stimulation therapy, the electrode for electrical stimulation therapy may include a first terminal that is provided at the second surface side of the first region of the sheet body, has a first socket, and is conductive to the reference electrode and one pair of second terminals that are provided at the second surface side of the second region of the sheet body, have second sockets facing the same direction as the first socket, and are conductive to the one pair of stimulating electrodes, the wiring member may include a composite wiring that incorporates at least a first wiring and one pair of second wirings, a first plug terminal that includes a terminal body provided at one end side of the composite wiring and having an opposing surface opposing the first socket and a first plug protruding from the opposing surface of the terminal body, being conductive to the first wiring, and being inserted into the first socket, and one pair of second plug terminals that are conductive to the one pair of second wirings and include second plugs to be inserted into the second sockets, the one pair of second wirings may pass through an interior of the terminal body and extend from the opposing surface of the terminal body, and the one pair of second plug terminals may be provided at tip portions of the one pair of second wirings.

According to this arrangement, since the electrode for electrical stimulation therapy of the present invention is included, the electrical stimulation therapeutic device with which the flat electrodes are unlikely to become detached even when the human body moves and with which the flat electrodes are easy to attach can be provided.

Also, in regard to the wiring member that connects the device body and the electrode for electrical stimulation therapy, at least the first wiring and the one pair of second wirings are incorporated in the composite wiring and the arrangement is one where the one pair of second wirings are branched from the first plug terminal. That is, a branched section of the one pair of second wirings can be restricted to a section between the first terminal and the second terminal of the sheet body. Consequently, the wirings are unlikely to interfere when attaching the flat electrodes to the human body and the flat electrodes can thus be attached more easily.

With the electrical stimulation therapeutic device according to the embodiment of the present invention, the one pair of second wirings may include one pair of connecting portions to the opposing surface of the terminal body and the one pair of connecting portions may be disposed to sandwich the first plug. Also, disconnection can be prevented as well.

According to this arrangement, since the first plug is sandwiched by the one pair of connecting portions, the first terminal is sandwiched by the one pair of connecting portions in a state where the wiring member is connected to the sheet body. Connection stability of the first plug with respect to the first terminal can thereby be improved.

The electrical stimulation therapeutic device according to the embodiment of the present invention may include a urination disorder treatment device.

BRIEF DESCRIPTION OF DRAWINGS

FIG. 22 is a perspective view showing a second modification example of the electrode for electrical stimulation therapy.

FIG. 23 is a right side view of the electrode for electrical stimulation therapy of FIG. 22.

DESCRIPTION OF EMBODIMENTS

Modes of implementing the present invention shall now be described with reference to the attached drawings.

Figure 1:
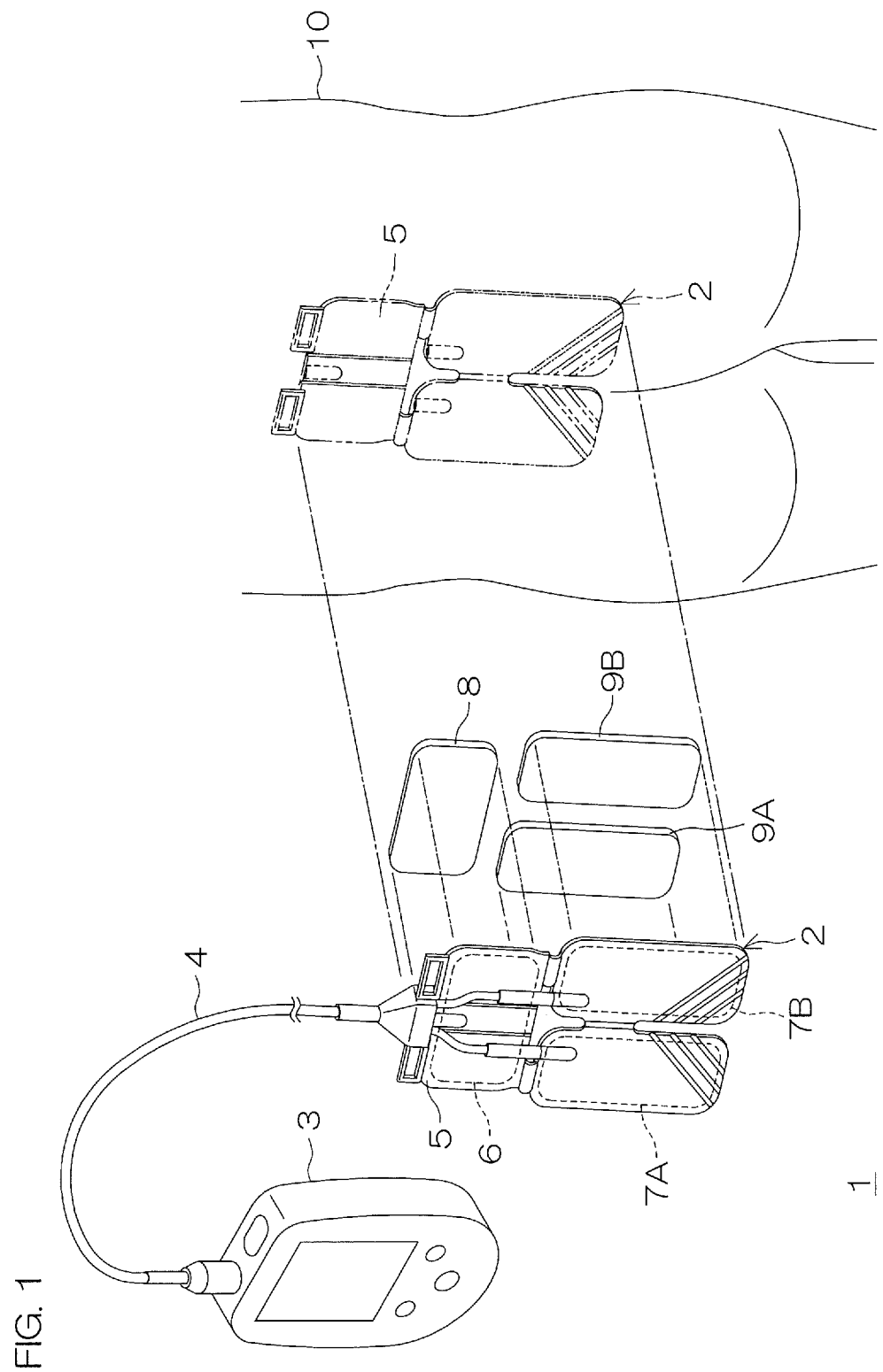
FIG. 1 is a perspective view of an electrical stimulation therapeutic device according to an embodiment of the present invention.

FIG. 1 is a perspective view of an electrical stimulation therapeutic device 1 according to an embodiment of the present invention.

<Overall Arrangement of Electrical Stimulation Therapeutic Device 1>

The electrical stimulation therapeutic device 1 is a device, for example, for improving urination disorder such as storage symptom (overactive bladder) by applying an electrical stimulation signal from a back side of the sacrum of a human body 10 (subject). Although with this embodiment, the electrical stimulation therapeutic device 1 as a urination disorder treatment device shall mainly be described, the electrical stimulation therapeutic device 1 also contributes to improvement not just of urination disorder but also of fecal incontinence such as impending fecal incontinence and passive fecal incontinence by electrical stimulus from the back side of the sacrum.

The electrical stimulation therapeutic device 1 includes an electrode 2 for electrical stimulation therapy, a device body 3, and a wiring cord 4 as an example of a wiring member of the present invention.

The electrode 2 includes a sheet body 5 and an reference electrode 6 and one pair of stimulating electrodes 7A and 7B as an example of at least one pair of flat electrodes of the present invention. Conductive adhesive pads 8, 9A, and 9B are adhered on the reference electrode 6 and the one pair of stimulating electrodes 7A and 7B, respectively. By one surface of each of the conductive adhesive pads 8, 9A, and 9B being adhered to a skin of the human body 10, the electrode 2 is fixed to the skin of the human body 10. In the present embodiment, the conductive adhesive pad 8 is adhered on the reference electrode 6, the conductive adhesive pad 9A is adhered on one stimulating electrode 7A, and the conductive adhesive pad 9B is adhered on the other stimulating electrode 7B.

The device body 3 is electrically connected to the electrode 2 by the wiring cord 4. A control circuit that includes, for example, a CPU, a memory such as a ROM or RAM, etc., a timer, etc., is incorporated in the device body 3. The subject can output an electrical signal (voltage) for outputting a current of a predetermined frequency to the electrode 2 by operating various operation buttons 11 and a touch panel 12 provided on the device body 3. Electrical stimulation is thereby applied to the human body 10 from the one pair of stimulating electrodes 7A and 7B of the electrode 2.

<Arrangement of Electrode 2>

Figure 2:
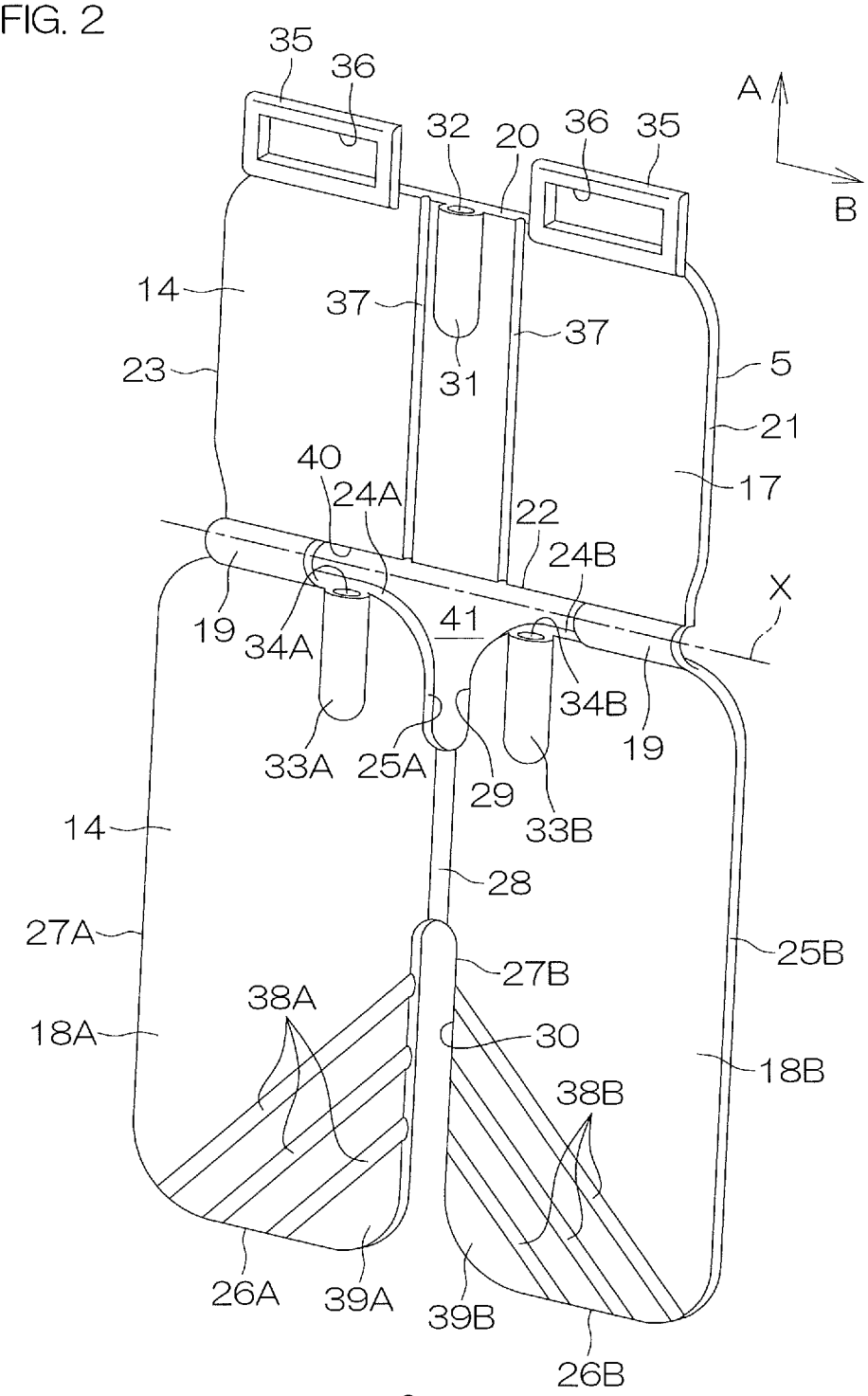
FIG. 2 is a perspective view of an electrode for electrical stimulation therapy according to an embodiment of the present invention.
Figure 3:
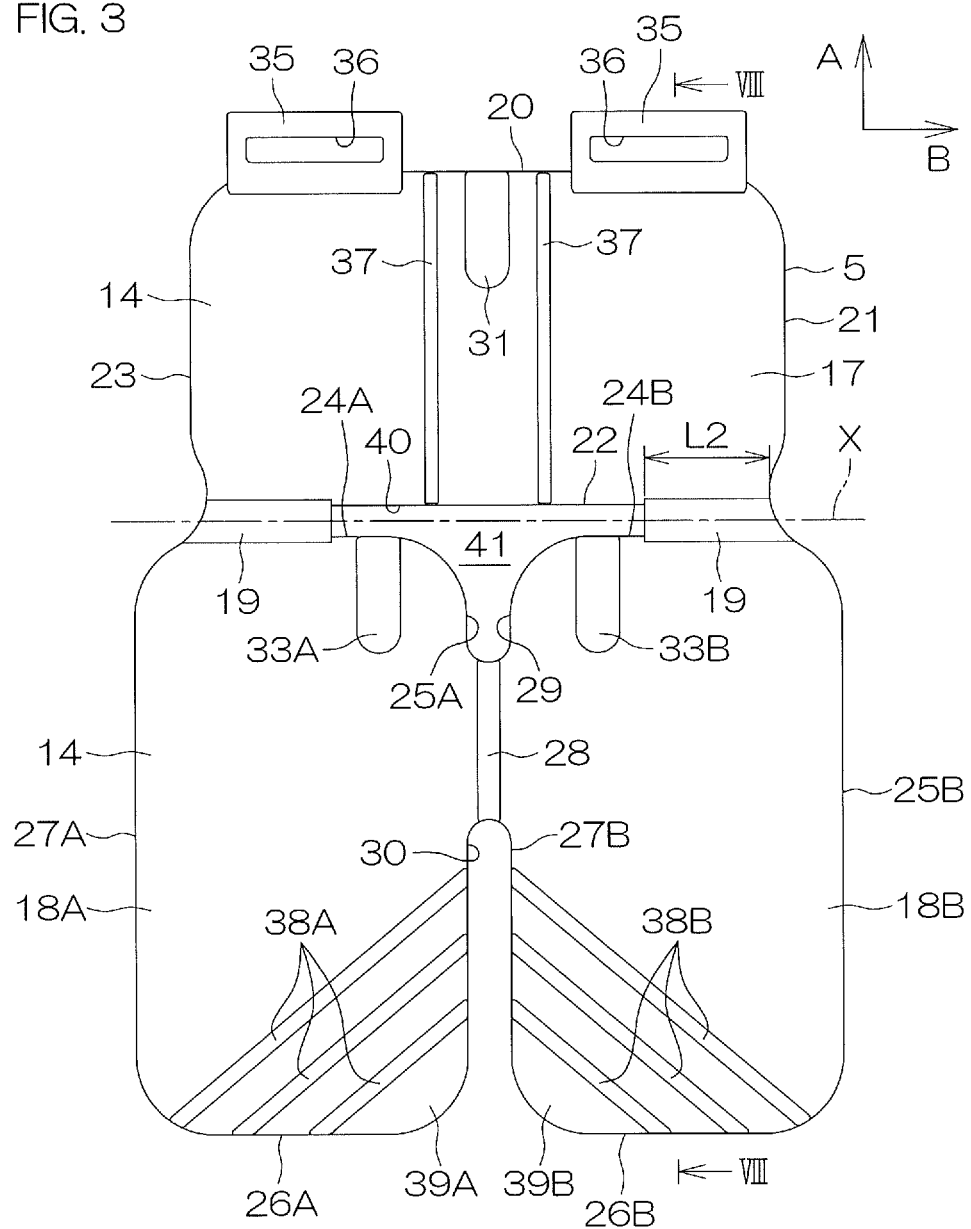
FIG. 3 is a front view of the electrode for electrical stimulation therapy according to the embodiment of the present invention.
Figure 4:
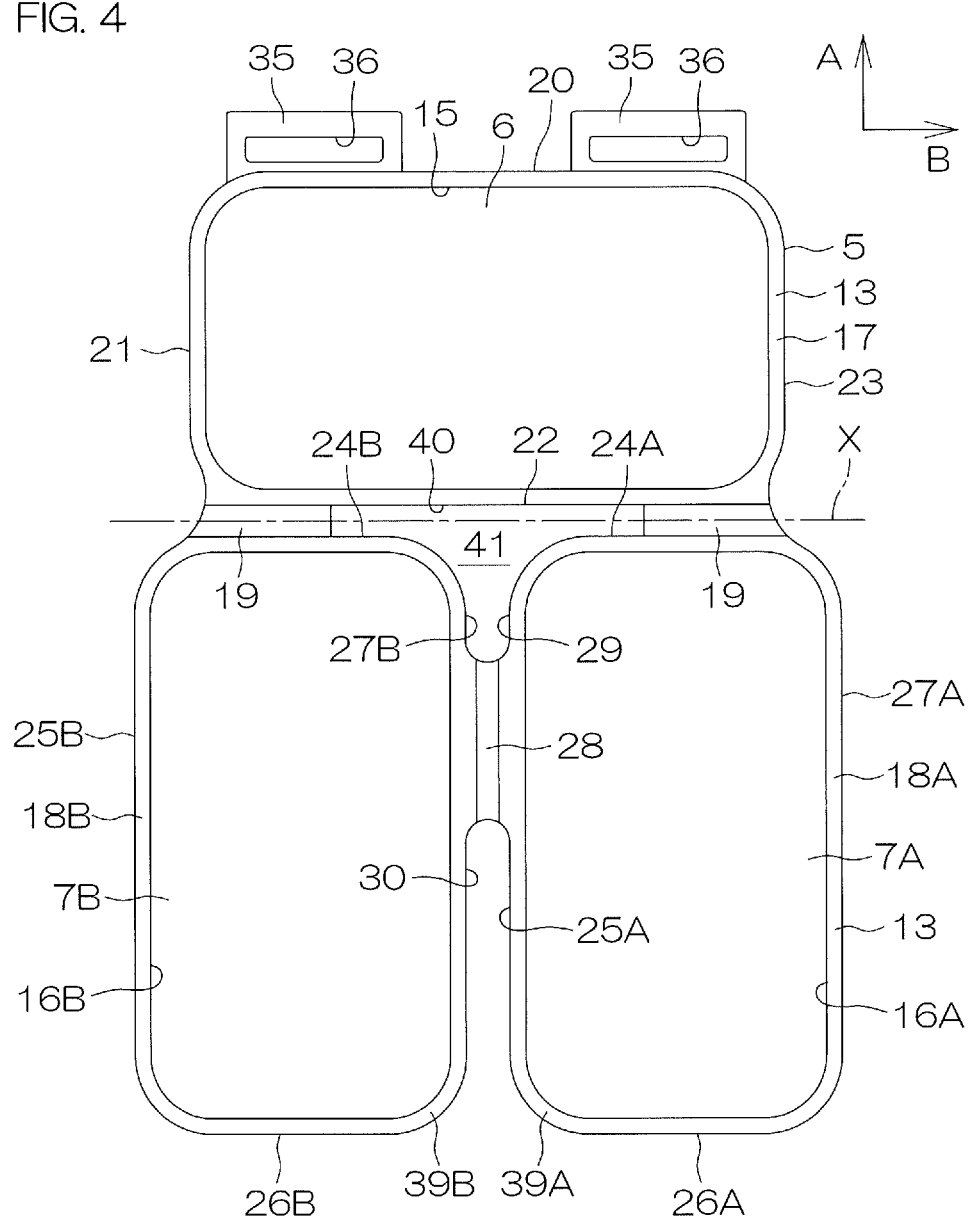
FIG. 4 is a back view of the electrode for electrical stimulation therapy according to the embodiment of the present invention.
Figure 5:
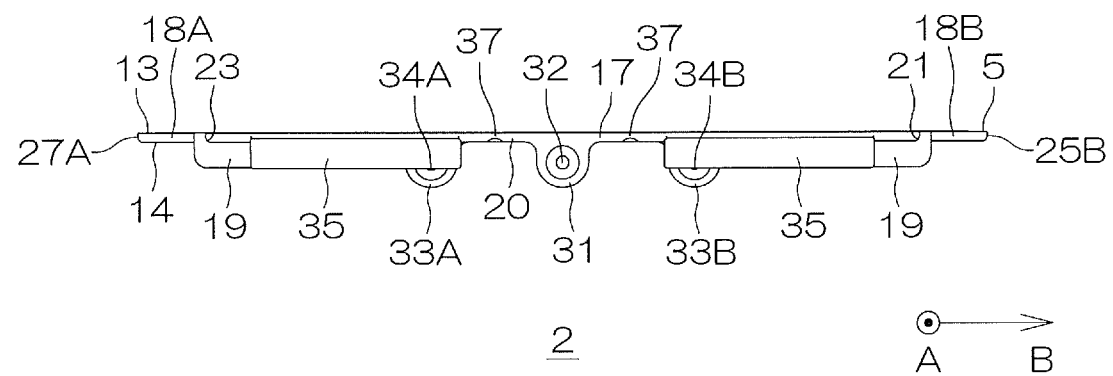
FIG. 5 is a plan view of the electrode for electrical stimulation therapy according to the embodiment of the present invention.
Figure 6:
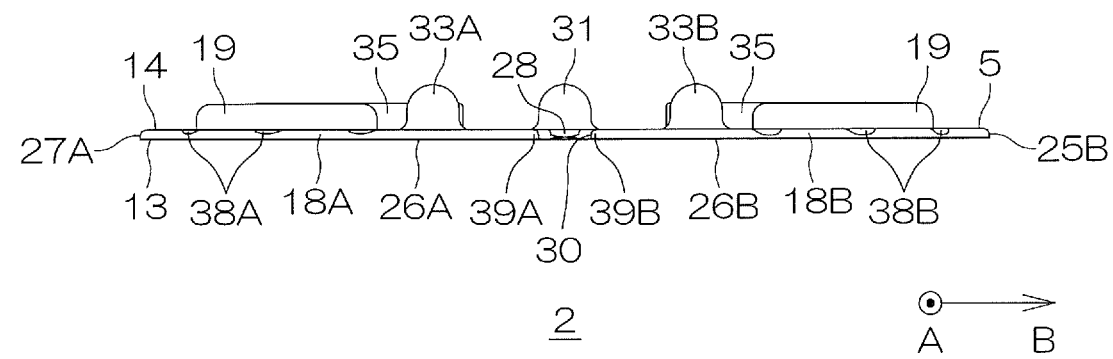
FIG. 6 is a bottom view of the electrode for electrical stimulation therapy according to the embodiment of the present invention.
Figure 7:
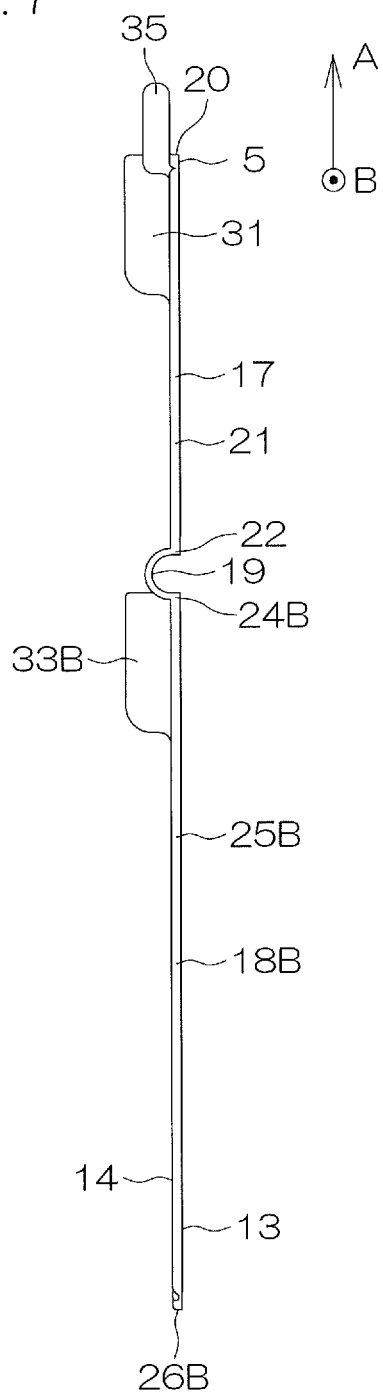
FIG. 7 is a right side view of the electrode for electrical stimulation therapy according to the embodiment of the present invention.
Figure 8:
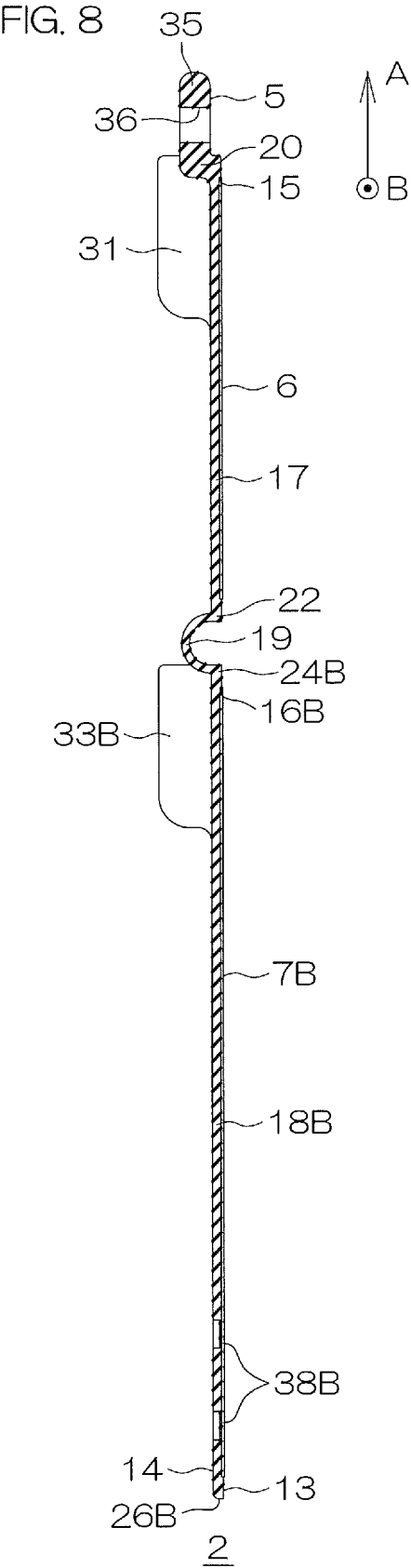
FIG. 8 is a sectional view of the electrode for electrical stimulation therapy according to the embodiment of the present invention and shows a section taken along VIII-VIII of FIG. 3.
Figure 9:
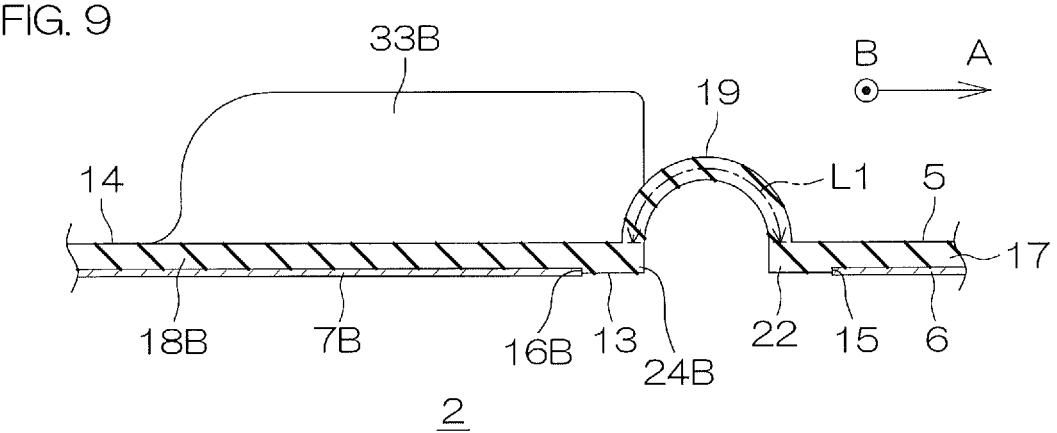
FIG. 9 is an enlarged view of a principal portion of FIG. 8.
Figure 10A:
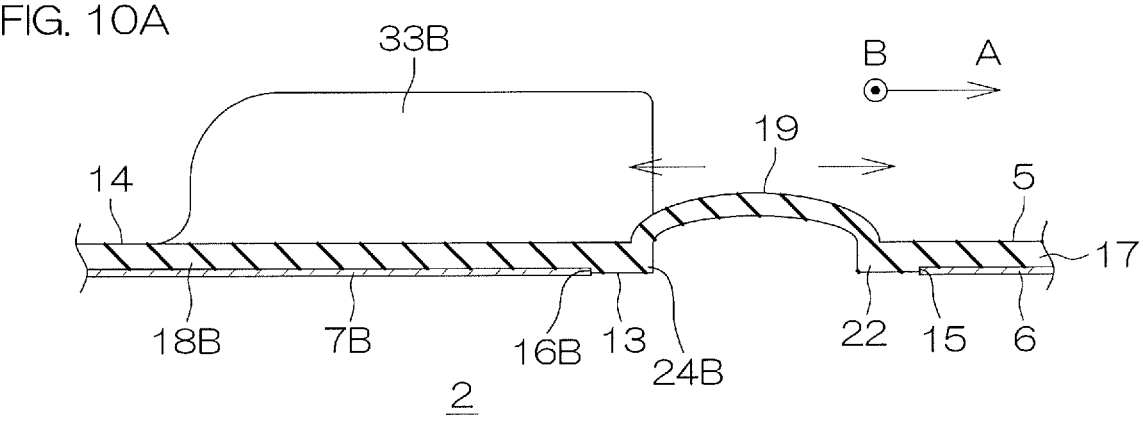
FIG. 10A and FIG. 10B are diagrams showing expanded and contracted states of an expandable/contractible portion of FIG. 9.
Figure 10B:
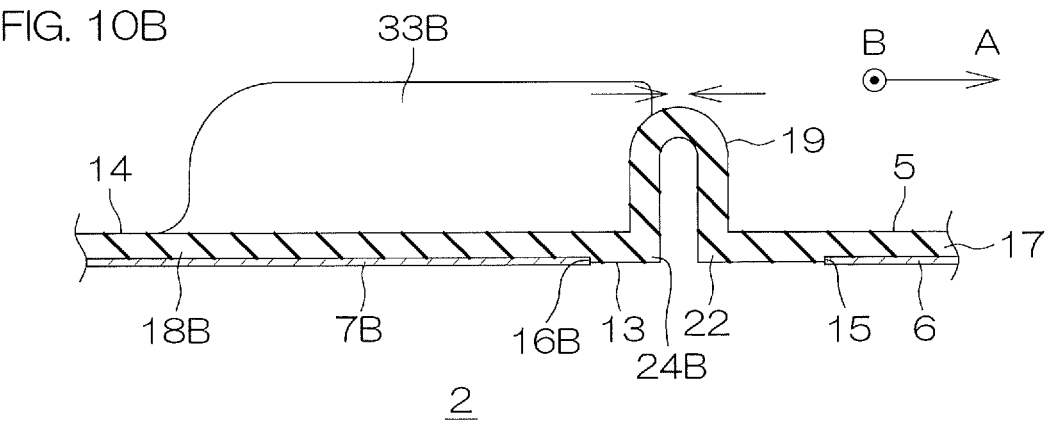

FIG. 2 is a perspective view of the electrode 2 for electrical stimulation therapy according to the embodiment of the present invention. FIG. 3 is a front view of the electrode for electrical stimulation therapy according to the embodiment of the present invention. FIG. 4 is a back view of the electrode 2 for electrical stimulation therapy according to the embodiment of the present invention. FIG. 5 is a plan view of the electrode 2 for electrical stimulation therapy according to the embodiment of the present invention. FIG. 6 is a bottom view of the electrode 2 for electrical stimulation therapy according to the embodiment of the present invention. FIG. 7 is a right side view of the electrode 2 for electrical stimulation therapy according to the embodiment of the present invention. FIG. 8 is a sectional view of the electrode 2 for electrical stimulation therapy according to the embodiment of the present invention and shows a section taken along VIII-VIII of FIG. 3. FIG. 9 is an enlarged view of a principal portion of FIG. 8. FIG. 10A and FIG. 10B are diagrams showing expanded and contracted states of an expandable/contractible portion 19 of FIG. 9. A left side view of the electrode 2 appears symmetrical to the right side view of FIG. 7 and shall thus be omitted.

As mentioned above, the electrode 2 includes the sheet body 5, the reference electrode 6, and the one pair of stimulating electrodes 7A and 7B.

The sheet body 5 is constituted of a material having flexibility that, when the human body 10 flexes (moves), is capable of curving in accordance with the flexing. In this embodiment, the sheet body 5 is constituted of a sheet member of flat shape having an insulating property and having a first surface 13 facing the skin of the human body 10 and a second surface 14 at an opposite side to the first surface 13.

Here, the sheet member of flat shape may be, for example, a member of sheet shape with a large portion being occupied by a region of thickness of 0.5 mm to 2.0 mm and may be provided partially with a structure of thickness exceeding the above range. Examples of such a structure include a first terminal 31, second terminals 33A and 33B, an assistive device attaching portions 35, etc., to be described below.

Insulating materials such as a resin film, nonwoven fabric, paper, etc., can be cited as examples of a material of the sheet body 5. Any of these may be used alone or two or more types may be used in combination. In this embodiment, the sheet body 5 is arranged from an integral, injection-molded sheet constituted of a silicone resin.

As shown in FIG. 3 and FIG. 4, the sheet body 5 is of a substantially quadrilateral shape as a whole. In this embodiment, the sheet body 5 is formed to be of a substantially quadrilateral shape with an upper side being slightly narrow in width when attached to the human body 10.

As shown in FIG. 4, FIG. 8, and FIG. 9, recesses 15, 16A, and 16B in which the reference electrode 6 and the one pair of stimulating electrodes 7A and 7B are respectively installed are formed in the first surface 13 of the sheet body 5. The reference electrode 6 and the one pair of stimulating electrodes 7A and 7B are respectively disposed in the recesses 15, 16A, and 16B. As shown in FIG. 9, the reference electrode 6 and the one pair of stimulating electrodes 7A and 7B (just the reference electrode 6 and the stimulating electrode 7B are shown in FIG. 9) may protrude further than the first surface 13 of the sheet body 5. That is, thicknesses of the reference electrode 6 and the one pair of stimulating electrodes 7A and 7B may be greater in comparison to depths of the recesses 15, 16A, and 16B.

The sheet body 5 is divided into two regions with a virtual axial line X (actually, an invisible line) extending between the reference electrode 6 and the one pair of stimulating electrodes 7A and 7B as a boundary. A region that is disposed at one side with respect to the virtual axial line X (in this embodiment, an upper side when the sheet body 5 is attached to the human body 10) and in which the reference electrode 6 is provided is a first region 17. Also, regions that are disposed at an opposite side to the first region 17 with respect to the virtual axial line X (in this embodiment, a lower side when the sheet body 5 is attached to the human body 10) and in which the one pair of stimulating electrodes 7A and 7B are provided are second regions 18A and 18B.

The first region 17 and the second regions 18A and 18B are coupled by expandable/contractible portions 19 and are opposed across the expandable/contractible portions 19 in a direction A intersecting the virtual axial line X (in this embodiment, a direction orthogonal to the virtual axial line X).

The first region 17 is of a substantially quadrilateral shape that is long (laterally long) in a direction B along the virtual axial line X. The first region 17 has a first end portion 20, a second end portion 21, a third end portion 22, and a fourth end portion 23 that constitute sides of a quadrilateral.

The first end portion 20 is, for example, an upper end portion of the first region 17 when the sheet body 5 is attached to the human body 10 and opposes the third end portion 22 in the direction A intersecting the virtual axial line X. In other words, the third end portion 22 is a lower end portion of the first region 17 when the sheet body 5 is attached to the human body 10. On the other hand, the second end portion 21 and the fourth end portion 23 extend along the direction A intersecting the virtual axial line X and couple the first end portion 20 and the third end portion 22. Also, the second end portion 21 and the fourth end portion 23 oppose each other in the direction B along the virtual axial line X.

With the first region 17, for example, a length in a lateral direction along the direction B along the virtual axial line X is approximately 5.3 cm and a length in a longitudinal direction along the direction A intersecting the virtual axial line X is approximately 9.5 cm.

The second regions 18A and 18B are each of a substantially quadrilateral shape that is long (longitudinally long) along the direction A intersecting the virtual axial line X. The respective second regions 18A and 18B have first end portions 24A and 24B, second end portions 25A and 25B, third end portions 26A and 26B, and fourth end portions 27A and 27B that constitute sides of quadrilaterals, respectively.

The first end portions 24A and 24B are, for example, upper end portions of the second regions 18A and 18B when the sheet body 5 is attached to the human body 10 and oppose the third end portions 26A and 26B in the direction A intersecting the virtual axial line X. In other words, the third end portions 26A and 26B are lower end portions of the second regions 18A and 18B when the sheet body 5 is attached to the human body 10. On the other hand, the second end portions 25A and 25B and the fourth end portions 27A and 27B extend along the direction A intersecting the virtual axial line X and couple the first end portions 24A and 24B and the third end portions 26A and 26B. Also, the second end portions 25A and 25B and the fourth end portions 27A and 27B oppose each other in the direction B along the virtual axial line X.

With each of the second regions 18A and 18B, for example, a length in the lateral direction along the direction B along the virtual axial line X is approximately 5.3 cm and a length in the longitudinal direction along the direction A intersecting the virtual axial line X is approximately 9.5 cm. That is, a total length in the lateral direction of the one pair of second regions 18A and 18B is longer than the length in the lateral direction of the first region 17. The sheet body 5 is thereby formed to be of the substantially quadrilateral shape with the upper side being slightly narrow in width when attached to the human body 10.

The one pair of second regions 18A and 18B are coupled to each other by a thin portion 28. The thin portion 28 is a portion of the sheet body 5 that is formed comparatively thinly and has a thickness, for example, of 0.3 mm to 2.0 mm. The thin portion 28 is a region of rectilinear shape (for example, having a width of approximately 32 mm) along the direction A intersecting the virtual axial line X and is formed at substantially a center of the second regions 18A and 18B in the direction A intersecting the virtual axial line X. Thereby, between the one pair of second regions 18A and 18B, slits 29 and 30 are respectively formed at one side (upper side) and another side (lower side) of the thin portion 28 in the direction A intersecting the virtual axial line X. In this embodiment, the slit 30 at the lower side is formed to be longer than the slit 29 at the upper side.

The first terminal 31 is provided integrally on the second surface 14 of the first region 17. As shown in FIG. 5 to FIG. 9, the first terminal 31 protrudes from the second surface 14 of the first region 17. As shown in FIG. 2, FIG. 5, and FIG. 6, the first terminal 31 is formed to a cylindrical shape that has a first socket 32 facing one side (upper side) in the direction A intersecting the virtual axial line X and is closed at another side (lower side) in the direction A intersecting the virtual axial line X.

In this embodiment, the first terminal 31 is formed such as to extend on an extension line of the thin portion 28 and such that the first socket 32 is flush with the first end portion 20 of the first region 17 as shown in FIG. 2 and FIG. 3. The first terminal 31 is made conductive to the reference electrode 6 at the first surface 13 side of the first region 17, for example, by an unillustrated lead wire.

The second terminals 33A and 33B are respectively provided integrally on the second surface 14 at the one pair of second regions 18A and 18B. As shown in FIG. 5 to FIG. 9, the second terminals 33A and 33B protrude from the second surface 14 at the second regions 18A and 18B. As shown in FIG. 2, FIG. 5, and FIG. 6, the second terminals 33A and 33B are formed to cylindrical shapes that have second sockets 34A and 34B facing the same direction as the first socket 32 and are closed at other sides (lower sides) in the direction A intersecting the virtual axial line X.

In this embodiment, the second terminals 33A and 33B are formed such as to be separated to inner sides of the second regions 18A and 18B from the slit 29 and such that the second sockets 34A and 34B are flush with the first end portions 24A and 24B of the second regions 18A and 18B as shown in FIG. 2 and FIG. 3. The second terminals 33A and 33B are made conductive to the one pair of stimulating electrodes 7A and 7B at the first surface 13 sides of the second regions 18A and 18B, for example, by unillustrated lead wires.

The assistive device attaching portions 35 are provided integrally on the first end portion 20 of the first region 17. The assistive device attaching portions 35 are portions to which an assistive device (for example, a belt, etc.) is attached, for example, when fixing the electrode 2 to the human body 10 and may, for example, be called belt loops when a belt is used as the assistive device.

In this embodiment, a total of two assistive device attaching portions 35 are provided, one each at respective ends of the first end portion 20 of the first region 17. The first terminal 31 is sandwiched by the one pair of assistive device attaching portions 35 in the direction B along the virtual axial line X. Each assistive device attaching portion 35 is formed to a quadrilateral annular shape having a slit 36 extending along the virtual axial line X and protrudes along a plane direction of the sheet body 5 from the second surface 14 at the first end portion 20.

Also, thin portions 37 are formed on the second surface 14 at the first region 17. The thin portions 37 are portions of the sheet body 5 that are formed comparatively thinly and have a thickness, for example, of 0.3 mm to 2.0 mm. The thin portions 37 include one pair of thin portions 37 that are regions of rectilinear shapes (for example, having a width of approximately 53 mm) along the direction A intersecting the virtual axial line X.

The one pair of thin portions 37 extend in parallel to each other from the first end portion 20 to the third end portion 22 of the first region 17 and are disposed to sandwich the first terminal 31 in between. The one pair of thin portions 37 are both separated from the first terminal 31 in the direction B along the virtual axial line X. By the one pair of thin portions 37 being formed, the sheet body 5 is formed to be easy to fold with the thin portions 37 as folds. The sheet body 5 can thereby be adhered satisfactorily in accordance with undulations of the skin of the human body 10.

Also, thin portions 38A and 38B are formed on the second surface 14 at the second regions 18A and 18B. The thin portions 38A and 38B are portions of the sheet body 5 that are formed comparatively thinly and have a thickness, for example, of 0.3 mm to 2.0 mm. The thin portions 38A and 38B respectively include pluralities of thin portions 38A and 38B that are regions of rectilinear shapes (for example, having a width of approximately 53 mm) extending from respective end portions of the second regions 18A and 18B opposing the slit 30 (for example, the second end portion 25A of the second region 18A and the fourth end portion 27B of the second region 18B) to the third end portions 26A and 26B.

The pluralities of thin portions 38A and 38B extend in parallel to each other from the respective end portions of the second regions 18A and 18B opposing the slit 30 up to the third end portions 26A and 26B. In this embodiment, three each of the thin portions 38A and 38B are formed as stripes.

By the pluralities of thin portions 38A and 38B being formed, the sheet body 5 is formed to be easy to fold with the thin portions 38A and 38B as folds. The sheet body 5 can thereby be adhered satisfactorily in accordance with the undulations of the skin of the human body 10. Also, the thin portions 38A and 38B of rectilinear shapes that link mutual end portions of the second regions 18A and 18B that are adjacent to each other with corner portions 39A and 39B at the slit 30 side as boundaries are formed and further, in this embodiment, are formed as stripes successively from the corner portions 39A and 39B toward inner regions. Therefore, by pinching the corner portions 39A and 39B with fingers, for example, after treatment, the sheet body 5 can be made easy to peel starting from the corner portions 39A and 39B.

In this embodiment, the expandable/contractible portions 19 include one pair of expandable/contractible portions 19 that are portions formed integral to the sheet body 5 and from the same material as the sheet body 5 and are mutually separated in the direction B along the virtual axial line X. More specifically, one of the one pair of expandable/contractible portions 19 couples the third end portion 22 of the first region 17 and the first end portion 24A of the second region 18A and the other of the one pair of expandable/contractible portions 19 couples the third end portion 22 of the first region 17 and the first end portion 24B of the second region 18B.

At the first end portion 24A of the second region 18A and the first end portion 24B of the second region 18B, the respective expandable/contractible portions 19 are disposed further outward than the second terminals 33A and 33B such as not to overlap with the second terminals 33A and 33B in the direction A intersecting the virtual axial line X. Second plugs 70A and 70B can thereby be made easy to insert into the second sockets 34A and 34B.

Each expandable/contractible portion 19 is formed along the virtual axial line X and, as shown in FIG. 8 and FIG. 9 and is bulgingly curved to the second surface 14 side of the sheet body 5 in a sectional view in the direction A intersecting the virtual axial line X. In this embodiment, the expandable/contractible portion 19 bulges in an arch shape to the second surface 14 side of the sheet body 5 in the sectional view and is formed to a substantially semicylindrical shape in a state where the sheet body 5 is flat. The expandable/contractible portion 19 of the arch shape has a flexibility of a degree such that it becomes recessed when pressed by a finger in a direction toward an interior from an apex portion of the arch. With the expandable/contractible portion 19 of the arch shape, a perimeter L1 in the sectional view shown in FIG. 9 is, for example, 1 cm to 3 cm. Also, a length L2 along the direction B along the virtual axial line X is, for example, 15 cm to 25 cm.

Here, the state where the sheet body 5 is flat may, for example, be a state where the sheet body 5 is not folded with the expandable/contractible portions 19 as folds and the first surface 13 at the first region 17 and the first surface 13 at the second regions 18A and 18B form the same plane or a state where the sheet body 5 is placed, for example, on a flat plane such that the first surface 13 sheet body 5 is a lower surface, etc. (the same applies hereinafter).

The expandable/contractible portion 19 has expandability/contractability and the expandability/contractability can be adjusted, for example, by increasing/decreasing a thickness of the expandable/contractible portion 19. For example, the thickness may be the same as or thinner than those of the first region 17 and the second regions 18A and 18B of the sheet body 5. In this embodiment, the expandable/contractible portion 19 is a portion of the sheet body 5 that is formed comparatively thinly and has a thickness, for example, of 0.3 mm to 2.0 mm.

The expandable/contractible portion 19 is thereby made freely expandable/contractible by expanding by a tensile force along the direction A intersecting the virtual axial line X being applied to the sheet body 5 (see FIG. 10A) and contracting by a compressive force along the direction A intersecting the virtual axial line X being applied to the sheet body 5 (see FIG. 10B).

Also, due to the one pair of expandable/contractible portions 19 being mutually separated in the direction B along the virtual axial line X, a slit 40 is formed between the first region 17 and the second regions 18A and 18B. The slit 40 is connected to the slit 29 between the second region 18A and the second region 18B. An opening 41 demarcated by the first region 17, the second regions 18A and 18B, and the one pair of expandable/contractible portions 19 is thereby formed in the sheet body 5. In this embodiment, the opening 41 is formed to a substantially T shape by the slit 29 that is long (extends) along the direction A intersecting the virtual axial line X and the slit 40 that is long (extends) along the direction B along the virtual axial line X.

Figure 14:
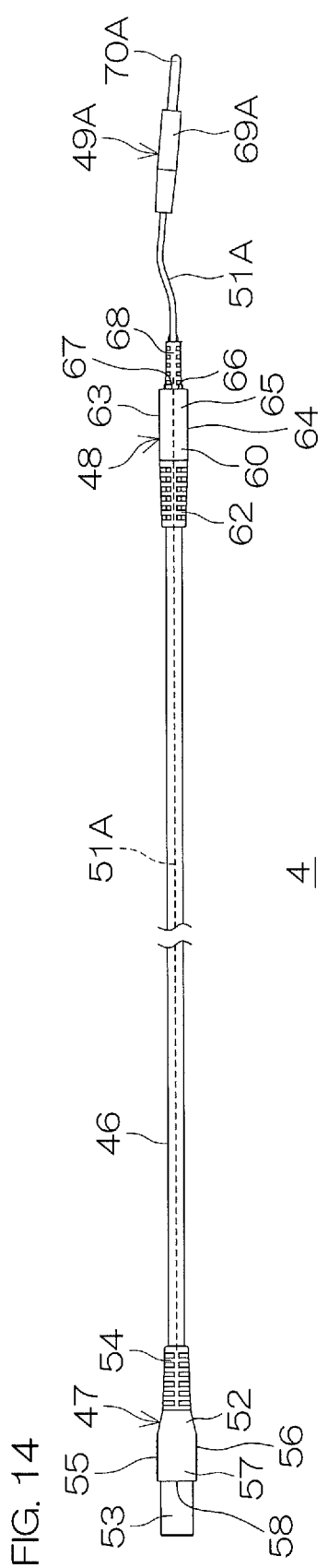
FIG. 14 is a side view of the wiring cord of FIG. 1.

The recess 15 is formed in the first surface 13 at the first region 17 and is formed to a substantially quadrilateral shape with corner portions being rounded as shown in FIG. 14. The reference electrode 6 is formed to substantially the same shape as the recess 15 and is disposed in the recess 15. Also, as examples of a material of the reference electrode 6, conductive materials such as silver paste, metal foil, carbon powder dispersed resin film, tin-doped indium oxide dispersed resin, etc., can be cited.

The recesses 16A and 16B are formed in the first surface 13 at the second regions 18A and 18B, respectively, and are formed to substantially quadrilateral shapes with corner portions being rounded as shown in FIG. 4. The one pair of stimulating electrodes 7A and 7B are formed to substantially the same shapes as the recesses 16A and 16B and are disposed in the recesses 16A and 16B. Also, as examples of a material of the one pair of stimulating electrodes 7A and 7B, the same materials as those for the reference electrode 6 can be cited.

To manufacture the electrode 2 such as described above, for example, the reference electrode 6 and the one pair of stimulating electrodes 7A and 7B are first molded by compression molding. Next, the obtained reference electrode 6 and one pair of stimulating electrodes 7A and 7B are inserted as insert members in a mold and the material of the sheet body 5 (in this embodiment, silicone resin) is made to fill the mold interior. The electrode 2 can thereby be obtained as an insert molded article.

However, a method for manufacturing the electrode 2 is not restricted to the insert molding described above and it may be a method where, for example, the reference electrode 6, the one pair of stimulating electrodes 7A and 7B, and the sheet body 5 are manufactured as separate molded articles and the reference electrode 6 and the one pair of stimulating electrodes 7A and 7B are thereafter respectively fitted into the recesses 15, 16A, and 16B of the sheet body 5.

<Arrangement of Conductive Adhesive Pads 8, 9A, and 9B>

The conductive adhesive pads 8, 9A, and 9B are arranged, for example, from a conductive adhesive gel for making a current output from the one pair of stimulating electrodes 7A and 7B flow in the human body 10. In this embodiment, the conductive adhesive pads 8, 9A, and 9B are arranged from pads having a thickness of approximately 0.8 mm.

Surfaces at both sides of the conductive adhesive pads 8, 9A, and 9B have an adhesive property. Surfaces at one side of the conductive adhesive pads 8, 9A, and 9B are adhered to the reference electrode 6 and the one pair of stimulating electrodes 7A and 7B and surfaces at the other side are adhered to the skin (treatment location) of the human body 10.

The conductive adhesive pads 8, 9A, and 9B have substantially the same shapes as the reference electrode 6 and the one pair of stimulating electrodes 7A and 7B, respectively. That is, the conductive adhesive pads 8, 9A, and 9B are formed to substantially quadrilateral shapes substantially matching the shapes of the reference electrode 6 and the one pair of stimulating electrodes 7A and 7B.

<Arrangement of Device Body 3>

Figure 11:
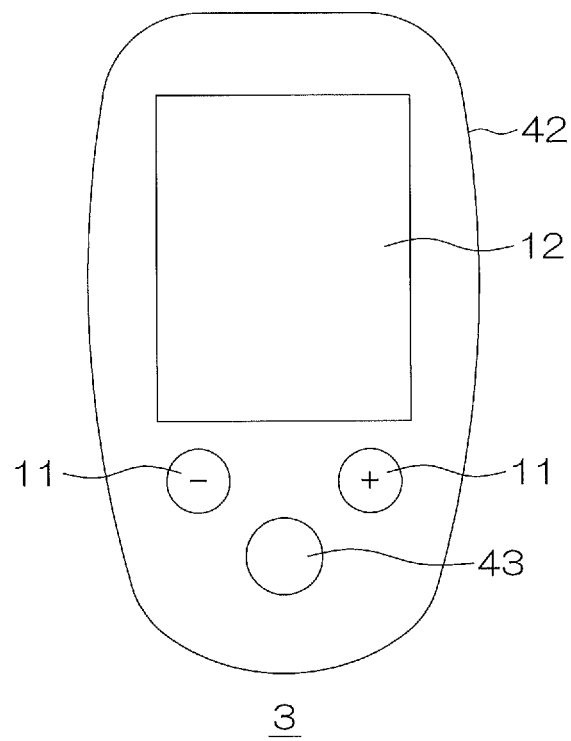
FIG. 11 is a front view of a device body of FIG. 1.
Figure 12:
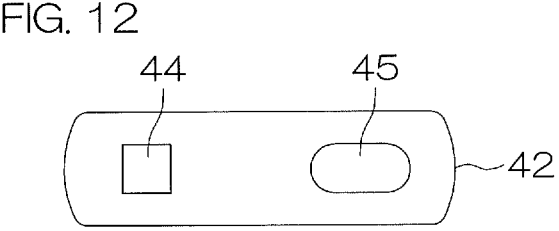
FIG. 12 is a plan view of the device body of FIG. 1.

FIG. 11 is a front view of the device body 3 of FIG. 1. FIG. 12 is a plan view of the device body 3 of FIG. 1.

The device body 3 includes a casing 42, a touch panel 12 provided on a front surface of the casing 42, a start/stop button 43 provided below the touch panel 12, and the plurality of operation buttons 11 and 11.

In this embodiment, the casing 42 is formed to a substantially elliptical shape and may be constituted, for example, of a case made of plastic. A first socket 44 and a second socket 45 are provided on an upper surface of the casing 42.

The first socket 44 is, for example, a port for output and the wiring cord 4 is connected thereto. On the other hand, the second socket 44 is, for example, a port for charging and a cord of an AC adapter (not shown) is connected thereto. That is, the device body 3 can be turned on by power supplied from a charged battery or from an electric outlet via the AC adapter.

The touch panel 12 is formed to a rectangular shape that is long along a length direction of the casing 42 and may be disposed near one end portion in the length direction of the casing 42. Also, the touch panel 12 may, for example, be a monochromatic or a color liquid crystal monitor. For example, a pulse waveform and a frequency of the electrical stimulation signal due to the one pair of stimulating electrodes 7A and 7B, an electrocardiographic waveform and a heart rate of the subject, an error message, etc., can be displayed on the touch panel 12. The subject can thereby easily know an operation state of the electrical stimulation therapeutic device 1.

The start/stop button 43 and the plurality of operation buttons 11 and 11 may be disposed at another end portion side in the length direction of the casing 42 with respect to the touch panel 12.

Also, an operation button 11 may have various functions depending on a device model of the electrical stimulation therapeutic device 1. For example, as a memory function of the electrical stimulation therapeutic device 1, a treatment menu that includes a width of a pulse wave (pulse width), a frequency, etc., of a stimulation signal appropriate for each of a plurality of subjects may be stored in the device body 3 and the button may be that which is operated to read it.

<Arrangement of Wiring Cord 4>

Figure 13:
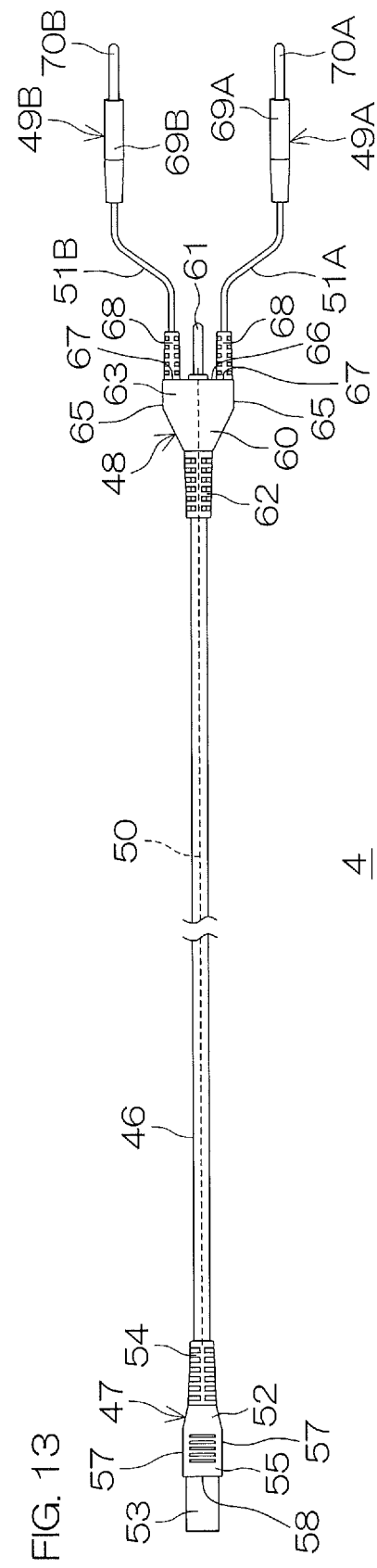
FIG. 13 is a plan view of a wiring cord of FIG. 1.
Figure 15:
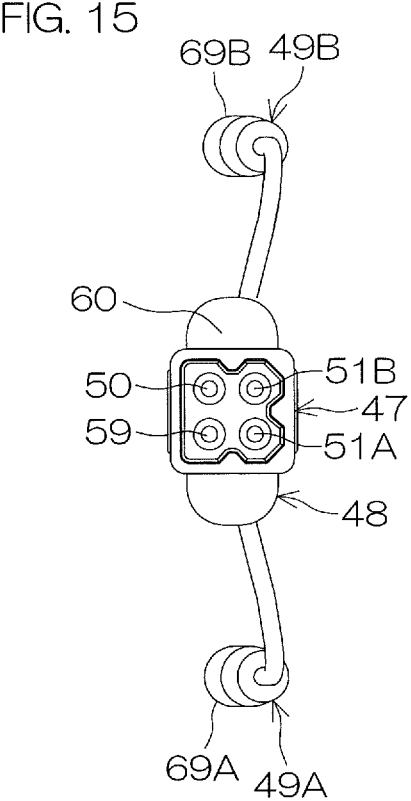
FIG. 15 is a front view of the wiring cord of FIG. 1.

FIG. 13 is a plan view of the wiring cord 4 of FIG. 1. FIG. 14 is a side view of the wiring cord 4 of FIG. 1. FIG. 15 is a front view of the wiring cord 4 of FIG. 1.

The wiring cord 4 includes a composite wiring 46, a power supply side plug terminal 47, a first plug terminal 48, and second plug terminals 49A and 49B.

The composite wiring 46 incorporates, for example, a first wiring 50 and one pair of second wirings 51A and 51B. The first wiring 50 and the one pair of second wirings 51A and 51B are each arranged by covering a conductor of wire shape with a protective film with an insulating property. The composite wiring 46 is arranged by bundling the first wiring 50 and the one pair of second wirings 51A and 51B into one and covering with a protective film with an insulating property.

Although among the first wiring 50 and the one pair of second wirings 51A and 51B, just the first wiring 50 is shown in FIG. 13 and just the second wiring 51A is shown in FIG. 14 due to lack of space, the first wiring 50 and the one pair of second wirings 51A and 51B are all incorporated in the same composite wiring 46.

The power supply side plug terminal 47 is provided at one end portion of the composite wiring 46. The power supply side plug terminal 47 includes a power supply side terminal body 52 and a power supply side plug 53.

The power supply side terminal body 52 is constituted, for example, of an injection molded article made of resin. The power supply side terminal body 52 is connected to the one end portion of the composite wiring 46 via a connecting portion 54, for example, of bellows shape. The power supply side terminal body 52 has an upper surface portion 55 and a lower surface portion 56 that define its thickness, one pair of side surface portions 57 and 57 that define its width, and a front surface portion 58 facing an opposite side to the connecting portion 54.

The power supply side plug 53 is constituted, for example, of an injection molded article made of resin that is integral to the power supply side terminal body 52 and protrudes from the front surface portion 58 of the power supply side terminal body 52. The power supply side plug 53 is formed, for example, to a substantially rectangular parallelepiped shape. As shown in FIG. 15, the first wiring 50 and the one pair of second wirings 51A and 51B are exposed inside the power supply side plug 53. Also, a dummy wiring 59 may be exposed inside the power supply side plug 53 in addition to the first wiring 50 and the one pair of second wirings 51A and 51B.

The first plug terminal 48 is provided at another end portion (end portion at an opposite side to the power supply side plug terminal 47) of the composite wiring 46. The first plug terminal 48 includes a first terminal body 60 and a first plug 61.

The first terminal body 60 is constituted, for example, of an injection molded article made of resin. The first terminal body 60 is connected to the other end portion of the composite wiring 46 via a connecting portion 62, for example, of bellows shape. The first terminal body 60 has an upper surface portion 63 and a lower surface portion 64 that define its thickness, one pair of side surface portions 65 and 65 that define its width, and a front surface portion 66 facing an opposite side to the connecting portion 62.

The first plug 61 is conductive to the first wiring 50 and is constituted, for example, of a metal plug. The first plug 61 protrudes from the front surface portion 66 of the first terminal body 60. In this embodiment, the first terminal body 60 is formed to a flat shape having a wide width in comparison with thickness and the first plug 61 protrudes from a width direction center of the front surface portion 66 of the first terminal body 60. Fixed wiring spaces 67 are formed at both sides in a width direction of the first plug 61.

The one pair of second wirings 51A and 51B that pass through interiors of the composite wiring 46 and the first terminal body 60 extend and are exposed from the wiring spaces 67. More specifically, at the front surface portion 66 of the first terminal body 60, connecting portions 66 of bellows shapes are provided one each in each of the wiring spaces 67 at both sides in the width direction of the first plug 61. That is, the one pair of connecting portions 68 are disposed at the front surface portion 66 of the first terminal body 60 such as to sandwich the first plug 61. The one pair of second wirings 51A and 51B extend in line shapes from the one pair of connecting portions 68 and the second plug terminals 49A and 49B are provided at tip portions thereof.

The second plug terminals 49A and 49B respectively include second terminal bodies 69A and 69B and second plugs 70A and 70B. The second terminal bodies 69A and 69B are constituted, for example, of injection molded articles made of resin. The second terminal bodies 69A and 69B are formed, for example, to substantially circular cylindrical shapes. The second plugs 70A and 70B are constituted, for example, of metal plugs and are conductive to the second wirings 51A and 51B.

<Method for Using Electrical Stimulation Therapeutic Device 1>

Figure 16:
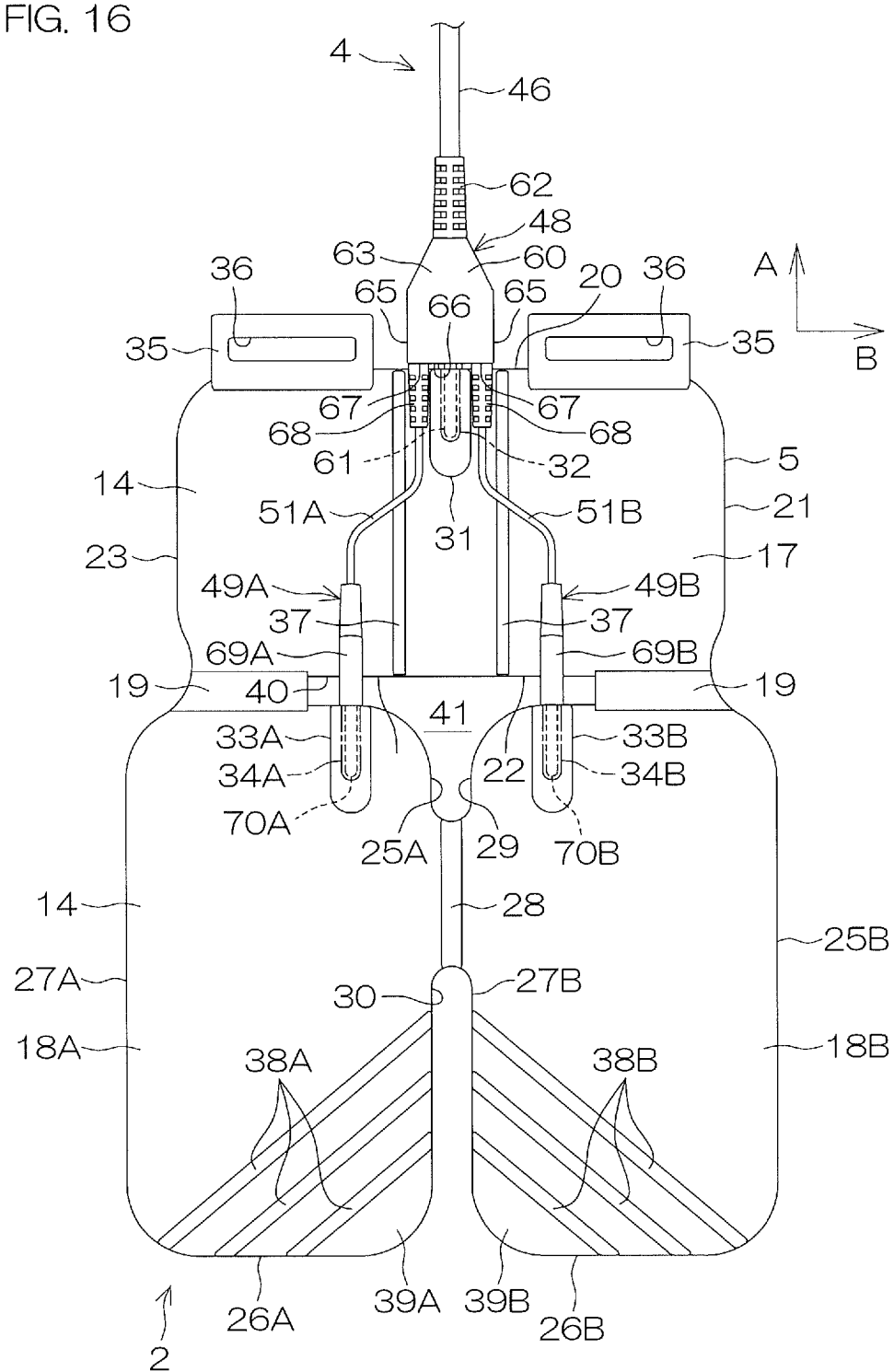
FIG. 16 is a diagram showing a connected state of the wiring cord with respect to the electrode.
Figure 17:
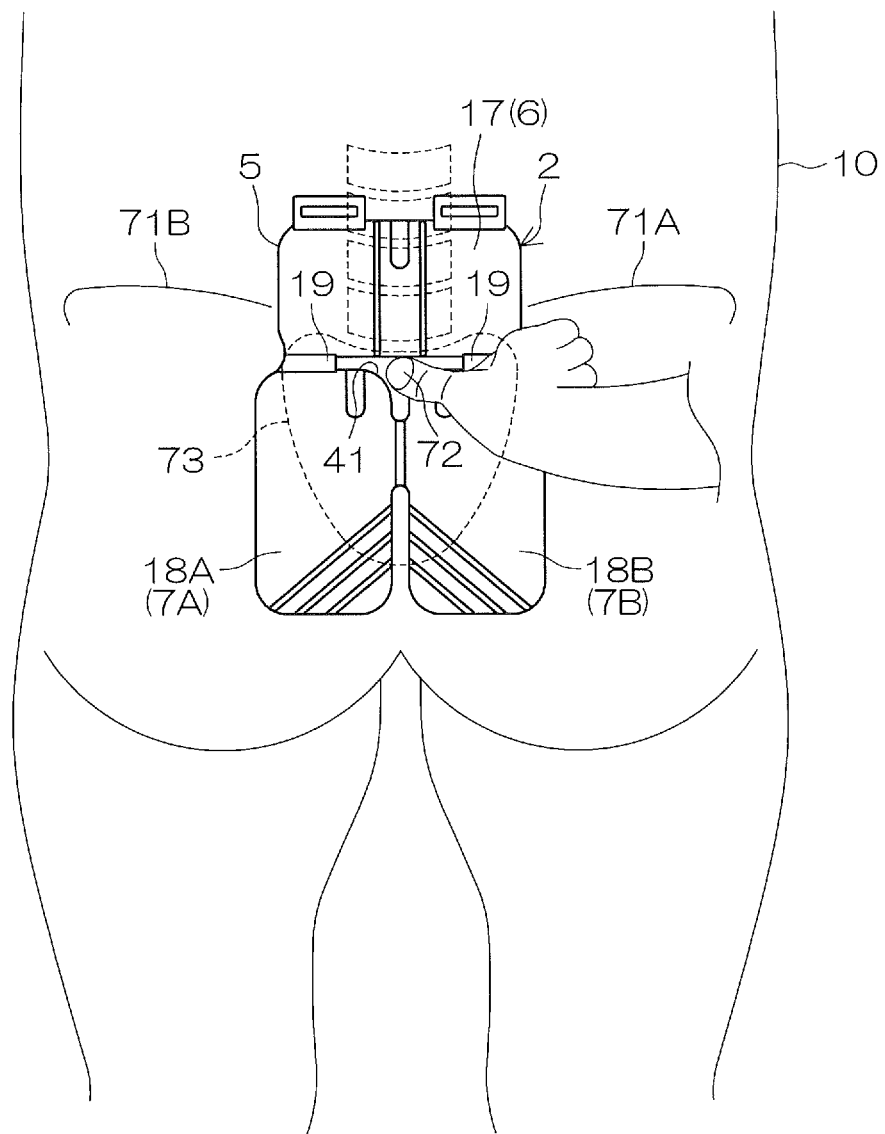
FIG. 17 is a diagram for describing a method for attaching the electrode to a human body.
Figure 18:
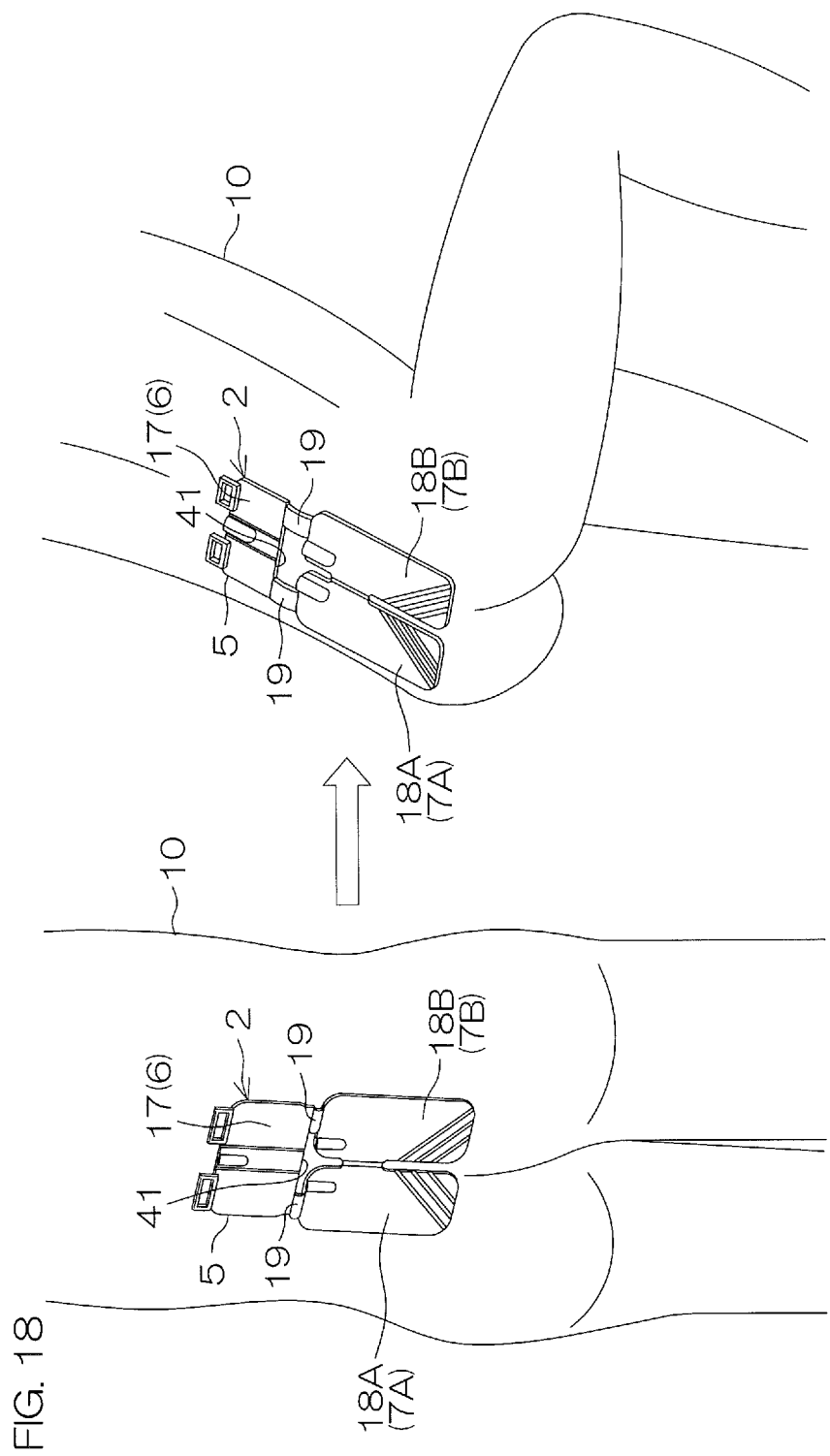
FIG. 18 is a diagram for describing an action and an effect of the electrode.

FIG. 16 is a diagram showing a connected state of the wiring cord 4 with respect to the electrode 2. FIG. 17 is a diagram for describing a method for attaching the electrode 2 to the human body 10. FIG. 18 is a diagram for describing an action and an effect of the electrode 2. In FIG. 17 and FIG. 18, an overall view of the wiring cord 4 and illustration of a portion of the electrode 2 are omitted for clarification of illustration.

To use the electrical stimulation therapeutic device 1, for example, first, the electrode 2 and the device body 3 are connected electrically.

To connect the electrode 2 and the device body 3 electrically, for example, the first plug 61 of the wiring cord 4 is inserted into the first socket 32 of the first terminal 31 as shown in FIG. 16. The first plug 61 is preferably inserted until the front surface portion 66 of the first terminal body 60 contacts the end surface of the first terminal 31. The first terminal 31 is thereby sandwiched by the one pair of connecting portions 68 at both sides of the first plug 61. Next, the second plugs 70A and 70B are respectively inserted into the second sockets 34A and 34B of the second terminals 33A and 33B. The electrode 2 and the wiring cord 4 are thereby connected.

On the other hand, the power supply side plug 53 of the wiring cord 4 is inserted into the first socket 44 of the device body 3. The device body 3 and the wiring cord 4 are thereby connected. Through the above work, electrical connection of the electrode 2 and the device body 3 is completed.

Next, the electrode 2 is adhered to the human body 10. More specifically, after adhering the conductive adhesive pads 8, 9A, and 9B to the reference electrode 6 and the one pair of stimulating electrodes 7A and 7B, for example, a thumb 72 is passed through the opening 41 of the electrode 2 and the thumb 72 is hooked onto the sheet body 5 as shown in FIG. 17. From this state, the thumb 72 is used to find an iliac crest 71A at a right side if one is right handed (an iliac crest 71B at a left side if one is left-handed). When the iliac crest 71A is found, the thumb 72 that is hooked onto the sheet body 5 is moved to a center of the back along the iliac crest 71A. Then, when the thumb 72 contacts a projection at the center of the back, since that position is a back side of a sacrum 73, the conductive adhesive pads 8, 9A, and 9B are adhered onto the skin.

Then, by operating the operation buttons 11 and the touch panel 12 of the device body 3 as appropriate to select a treatment menu and pressing the start/stop button 43, current can be made to flow from the one pair of stimulating electrodes 7A and 7B adhered to the back side of the sacrum 73.

Since positioning of the reference electrode 6 and the one pair of stimulating electrodes 7A and 7B can thus be performed with a finger being hooked on the sheet body 5 by passing the finger through the opening 41, the reference electrode 6 and the one pair of stimulating electrodes 7A and 7B can be attached extremely easily. Also, when positioning the reference electrode 6 and the one pair of stimulating electrodes 7A and 7B, the position of the sacrum can be found by being guided by the finger that is passed through the opening 41, an appropriate attachment position of the electrode 41 can thus be found easily even when visual observation or visual recognition through a mirror is not possible. Further, since the position of the sheet body 5 can be finely adjusted with the finger passed through the opening 41 as a support point, the positioning can be performed more easily.

Also, the first wiring 50 and the one pair of second wirings 51A and 51B are incorporated in the composite wiring 46 and the arrangement is one where the one pair of second wirings 51A and 51B are branched from the first plug terminal 48. That is, as shown in FIG. 16, a branched section of the one pair of second wirings 51A and 51B can be restricted to a section between the first terminal 31 and the second terminals 33A and 33B of the sheet body 5. Consequently, the wirings are unlikely to interfere when attaching the electrode 2 to the human body 10 and the electrode 2 can thus be attached more easily. Also, disconnection can be prevented as well.

Also, since the first terminal 31 of the sheet body 5 is sandwiched by the one pair of connecting portions 68 as shown in FIG. 16, connection stability of the first plug 61 with respect to the first terminal 31 can be improved.

Further, with this electrical stimulation therapeutic device 1, the sheet body 5 of the electrode 2 includes the expandable/contractible portions 19. Therefore, even if the reference electrode 6 and the one pair of stimulating electrodes 7A and 7B are attached, for example, across a flexing portion of the human body 10 (a vicinity of the waist in this embodiment), application of an excessive force in a plane direction on the reference electrode 6 and the one pair of stimulating electrodes 7A and 7B when the human body 10 flexes (moves) can be suppressed by the expandable/contractible portions 19 expanding or contracting in accordance with the flexing.

For example, when, as shown in FIG. 18, the human body 10 flexes from a standing posture to a squatting posture, application of an excessive force in a plane direction on the reference electrode 6 and the one pair of stimulating electrodes 7A and 7B can be suppressed by the expandable/contractible portions 19 expanding. Consequently, the reference electrode 6 and the one pair of stimulating electrodes 7A and 7B can be made unlikely to become detached from the human body 10.

Also, if, as in this embodiment, the expandable/contractible portions 19 are of the arch shapes in the sectional view, the expandable/contractible portions 19 can be made to expand/contract smoothly and therefore, the application of an excessive force in a plane direction on the reference electrode 6 and the one pair of stimulating electrodes 7A and 7B can be suppressed further. Further, with the expandable/contractible portions 19 of arch shapes, the perimeter L1 shown in FIG. 9 is preferably 1 cm to 3 cm in the sectional view. If the perimeter L1 is within this range, electrode peeling can be suppressed regardless of body shape of the human body 10 and since the expandable/contractible portions 19 will also not protrude excessively, electrode peeling due to unexpectedly contacting the expandable/contractible portions 19 can also be suppressed.

<First Modification Example of Electrode 2>

Figure 19:
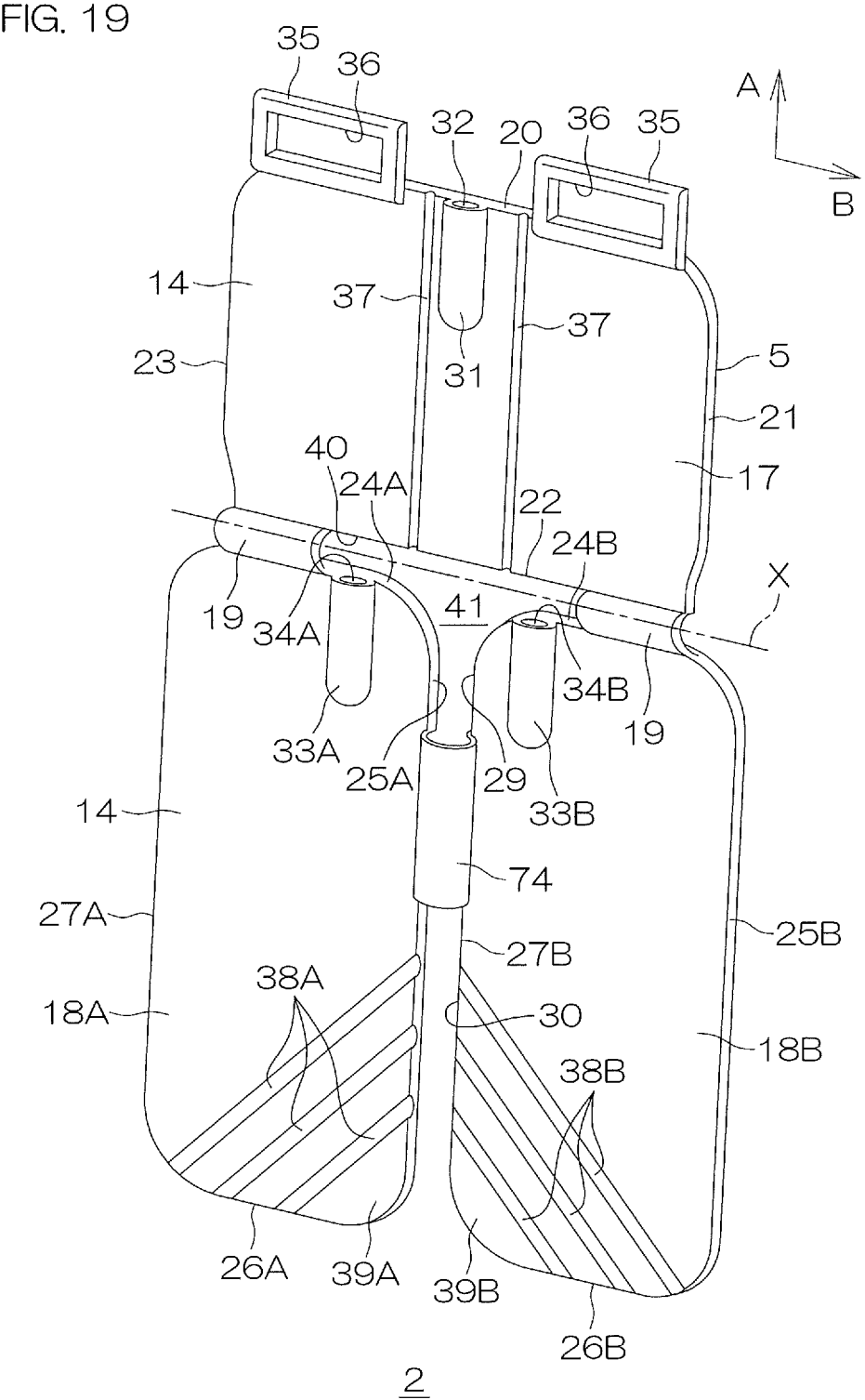
FIG. 19 is a perspective view showing a first modification example of the electrode for electrical stimulation therapy.
Figure 20:
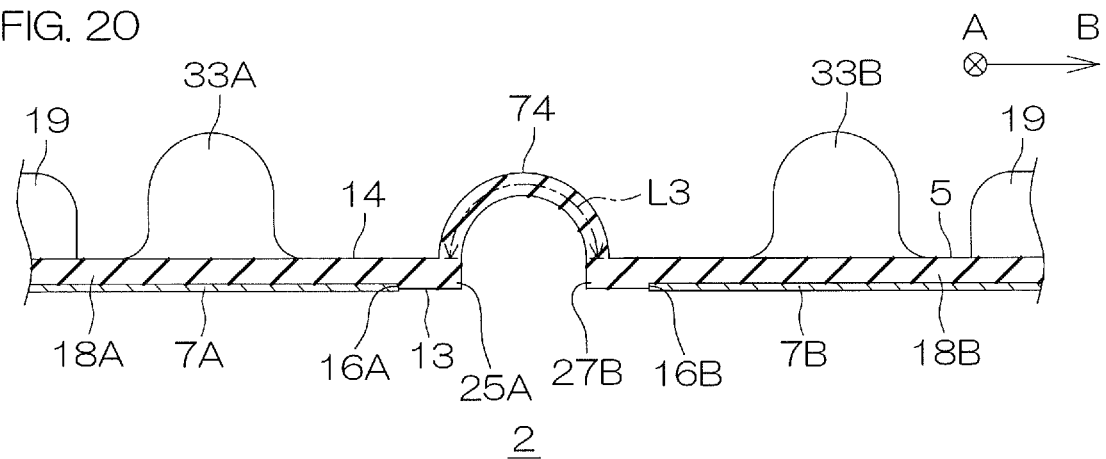
FIG. 20 is a sectional view of the electrode for electrical stimulation therapy of FIG. 19.
Figure 21A:
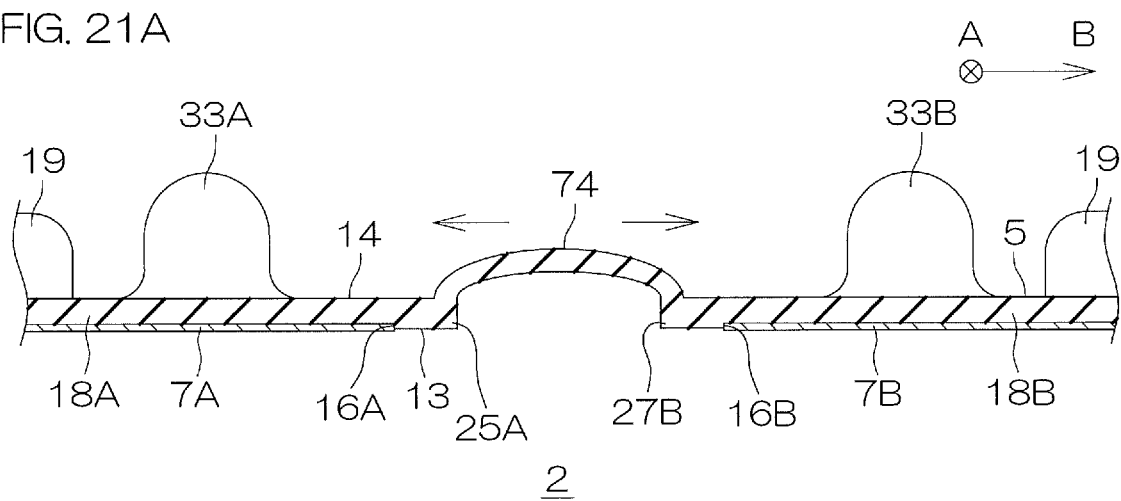
FIG. 21A and FIG. 21B are diagrams showing expanded and contracted states of a second expandable/contractible portion of FIG. 19 and FIG. 20.
Figure 21B:
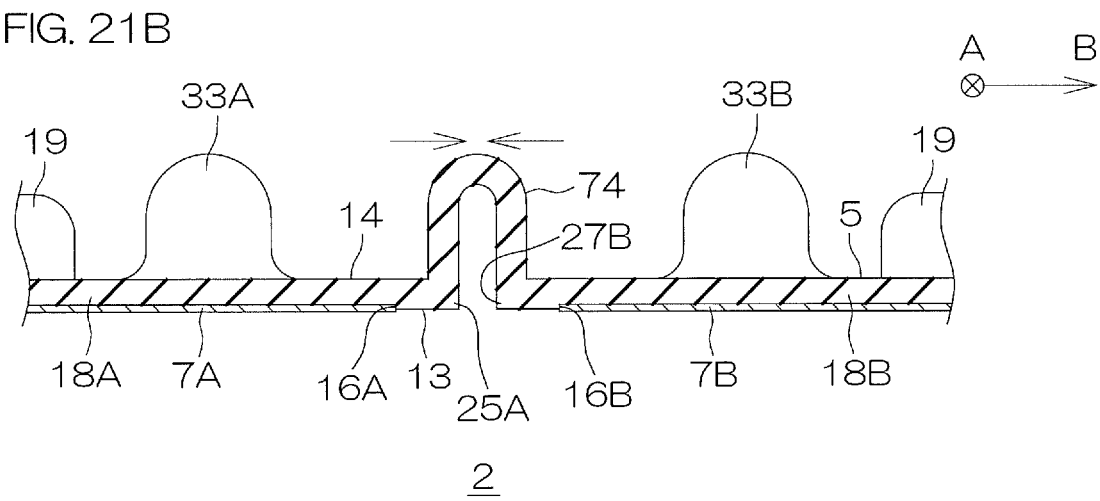

FIG. 19 is a perspective view showing a first modification example of the electrode 2 for electrical stimulation therapy. FIG. 20 is a sectional view of the electrode 2 for electrical stimulation therapy of FIG. 19. FIG. 21A and FIG. 21B are diagrams showing expanded and contracted states of a second expandable/contractible portion 74 of FIG. 19 and FIG. 20.

Although as described above, the one pair of second regions 18A and 18B of the sheet body 5 may be coupled to each other by the thin portion 28, these may be coupled by the second expandable/contractible portion 74 instead as shown in FIG. 19.

The second expandable/contractible portion 74 is a portion that is formed integral to the sheet body 5 and from the same material as the sheet body 5. The second expandable/contractible portion 74 is formed to a rectilinear shape along the direction A intersecting the virtual axial line X and is formed at substantially the center of the second regions 18A and 18B in the direction A intersecting the virtual axial line X.

As shown in FIG. 20, the second expandable/contractible portion 74 is bulgingly curved to the second surface 14 side of the sheet body 5 in a sectional view in the direction B along the virtual axial line X. In this embodiment, the second expandable/contractible portion 74 bulges in an arch shape to the second surface 14 side of the sheet body 5 in the sectional view and is formed to a substantially semicylindrical shape in a state where the sheet body 5 is flat. With the second expandable/contractible portion 74 of the arch shape, a perimeter L3 in the sectional view shown in FIG. 20 is, for example, 1 cm to 3 cm.

The second expandable/contractible portion 74 has expandability/contractability and the expandability/contractability can be adjusted, for example, by increasing/decreasing a thickness of the second expandable/contractible portion 74. For example, the thickness may be the same as or thinner than those of the first region 17 and the second regions 18A and 18B of the sheet body 5. In this embodiment, the second expandable/contractible portion 74 is a portion of the sheet body 5 that is formed comparatively thinly and has a thickness, for example, of 0.3 mm to 2.0 mm.

The second expandable/contractible portion 74 is thereby made freely expandable/contractible by expanding by a tensile force along the direction B along the virtual axial line X being applied to the sheet body 5 (see FIG. 21A) and contracting by a compressive force along the direction B along the virtual axial line X being applied to the sheet body 5 (see FIG. 21B).

As described above, with the arrangement of FIG. 19, FIG. 20, and FIGS. 21A and B, since the second expandable/contractible portion 74 expands/contracts, for example, when the positioning of the electrode 2 is performed as shown in FIG. 17, fine adjustment of the position in the direction B along the virtual axial line X can be performed easily. In FIG. 17, fine adjustment of the position in the right/left direction of the human body 10 can be performed easily.

<Second Modification Example of Electrode 2>

FIG. 22 is a perspective view showing a second modification example of the electrode 2 for electrical stimulation therapy. FIG. 23 is a right side view of the electrode 2 for electrical stimulation therapy of FIG. 22.

The electrode 2 of the second modification example includes expandable/contractible portions 79 in place of the expandable/contractible portions 19 that are bulgingly curved to the second surface 14 side of the sheet body 5 in the sectional view in the direction A intersecting the virtual axial line X.

The expandable/contractible portions 79 are constituted of an elastic material and are formed to flat shapes along the second surface 14 of the sheet body 5. Here, the flat shapes along the second surface 14 mean that, unlike the expandable/contractible portions 19, both surfaces of each flat expandable/contractible portion 79 that has one surface 80 and another surface 81 at an opposite side thereto do not protrude from either of the first surface 13 and the second surface 14 of the sheet body 5 when the sheet body 5 is in a flat state.

As a material of the expandable/contractible portions 79, for example, a flat rubber material, etc., that has expandability/contractability can be applied.

As shown in FIG. 22, the expandable/contractible portions 79 include one pair of expandable/contractible portions 79 that are mutually separated in the direction B along the virtual axial line X. One of the one pair of expandable/contractible portions 79 couples the third end portion 22 of the first region 17 and the first end portion 24A of the second region 18A and the other of the one pair of expandable/contractible portions 79 couples the third end portion 22 of the first region 17 and the first end portion 24B of the second region 18B. Each expandable/contractible portion 79 may have a fixed thickness from one end to another end in the direction B along the virtual axial line X.

To manufacture the electrode 2 such as described above, for example, the reference electrode 6 and the one pair of stimulating electrodes 7A and 7B are first molded by compression molding. Next, the obtained reference electrode 6 and one pair of stimulating electrodes 7A and 7B and the elastic material for the expandable/contractible portions 79 that has been prepared separately are inserted as insert members in a mold and the material of the sheet body 5 (in this embodiment, silicone resin) is made to fill the mold interior. The electrode 2 can thereby be obtained as an insert molded article.

The electrode 2 of this second modification example includes the expandable/contractible portions 79. Therefore, when, as shown in FIG. 18, the human body 10 flexes (moves), the material (elastic material) of the expandable/contractible portions 79 expands/contracts in accordance with the flexing. Application of an excessive force in a plane direction on the reference electrode 6 and the one pair of stimulating electrodes 7A and 7B can thereby be suppressed.

<Third Modification Example of Electrode 2>

Figure 24:
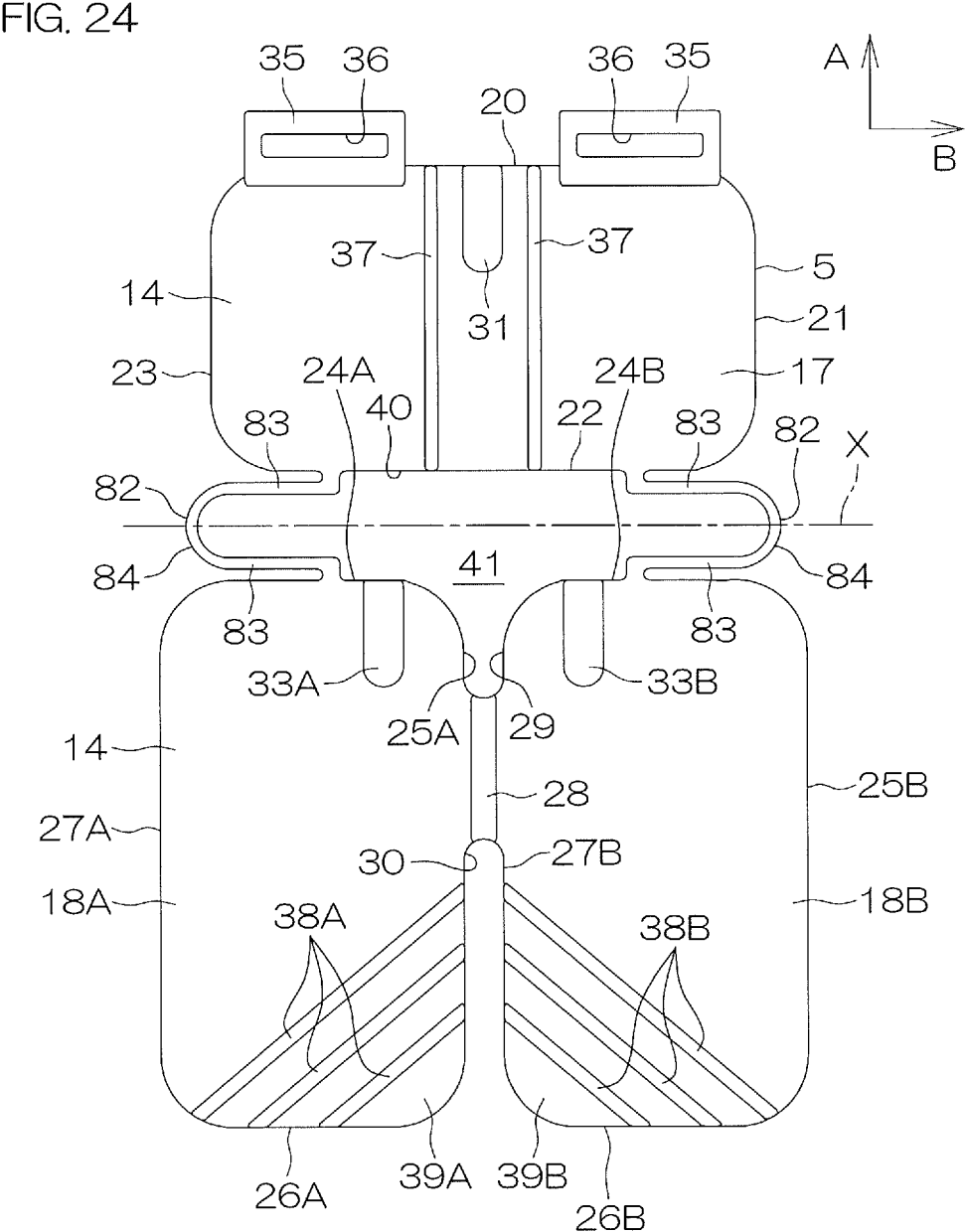
FIG. 24 is a front view showing a third modification example of the electrode for electrical stimulation therapy.
Figure 25:
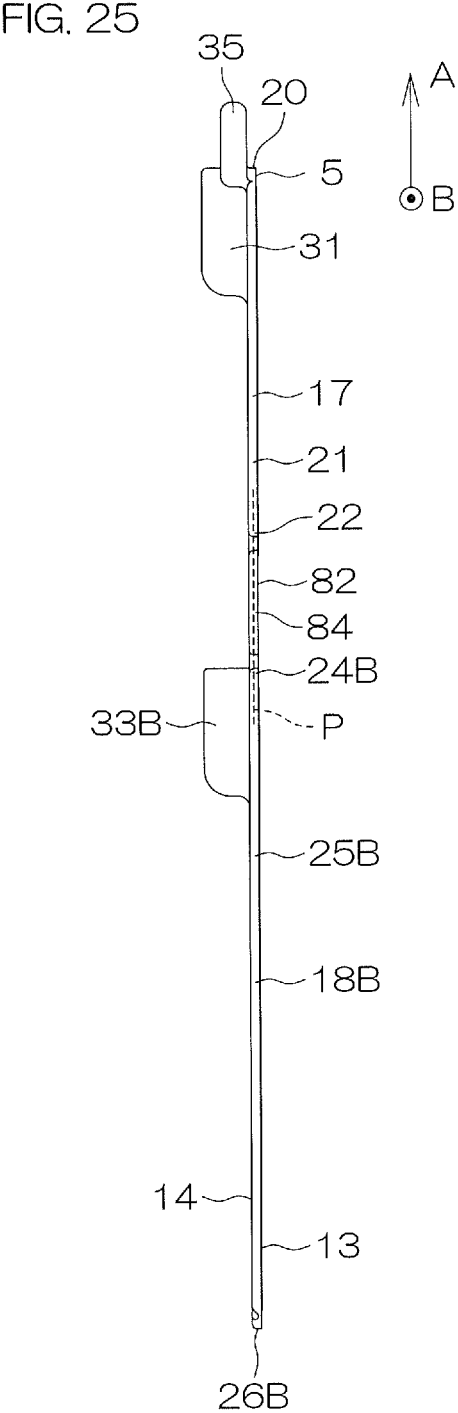
FIG. 25 is a right side view of the electrode for electrical stimulation therapy of FIG. 24.

FIG. 24 is a front view showing a third modification example of the electrode 2 for electrical stimulation therapy. FIG. 25 is a right side view of the electrode 2 for electrical stimulation therapy of FIG. 24.

The electrode 2 of the third modification example includes expandable/contractible portions 82 in place of the expandable/contractible portions 19 that are bulgingly curved to the second surface 14 side of the sheet body 5 in the sectional view in the direction A intersecting the virtual axial line X.

As shown in FIG. 24, the expandable/contractible portions 82 include one pair of expandable/contractible portions 82 that are mutually separated in the direction B along the virtual axial line X. One of the one pair of expandable/contractible portions 82 couples the third end portion 22 of the first region 17 and the first end portion 24A of the second region 18A and the other of the one pair of expandable/contractible portions 82 couples the third end portion 22 of the first region 17 and the first end portion 24B of the second region 18B. Each expandable/contractible portion 82 is of a folded line shape when the second surface 14 of the sheet body 5 is viewed from above.

More specifically, each expandable/contractible portion 82 includes one pair of first portions 83 extending along the direction B along the virtual axial line X and a second portion 84 extending along the direction A intersecting the virtual axial line X and coupling mutual one end portions of the one pair of first portions 83. Mutual other end portions of the one pair of first portions 83 are mutually separated in the direction A intersecting the virtual axial line X. In this third modification example, the expandable/contractible portions 82 are folded to a U shape in a region between the first region 17 and the second regions 18A and 18B.

Also, as shown in FIG. 25, the expandable/contractible portions 82 extend on a plane along the second surface 14 of the sheet body 5. Here, to extend on a plane along the second surface 14 means that, when the sheet body 5 is in the flat state, the expandable/contractible portions 82 do not protrude from either of the first surface 13 and the second surface 14 of the sheet body 5 and are disposed on a plane P parallel to the second surface 14 of the sheet body 5.

To manufacture the electrode 2 such as described above, for example, the reference electrode 6 and the one pair of stimulating electrodes 7A and 7B are first molded by compression molding. Next, the obtained reference electrode 6 and one pair of stimulating electrodes 7A and 7B are inserted as insert members in a mold and the material of the sheet body 5 (in this embodiment, silicone resin) is made to fill the mold interior. The electrode 2 can thereby be obtained as an insert molded article.

The electrode 2 of this third modification example includes the expandable/contractible portions 82 of U shapes. Therefore, when, as shown in FIG. 18, the human body 10 flexes (moves), each expandable/contractible portion 82 expands/contracts by the one pair of first portions 83 separating or approaching in accordance with the flexing.

Application of an excessive force in a plane direction on the reference electrode 6 and the one pair of stimulating electrodes 7A and 7B can thereby be suppressed.

Also, end portions of the one pair of first portions 83 that are coupled by the second portion 84 are each positioned at an opposite side to the other expandable/contractible portion 82, that is, at an outer side. The shape of the sheet body 5 coupled by the expandable/contractible portions 82 can thereby be held with stability.

<Fourth Modification Example of Electrode 2>

Figure 26:
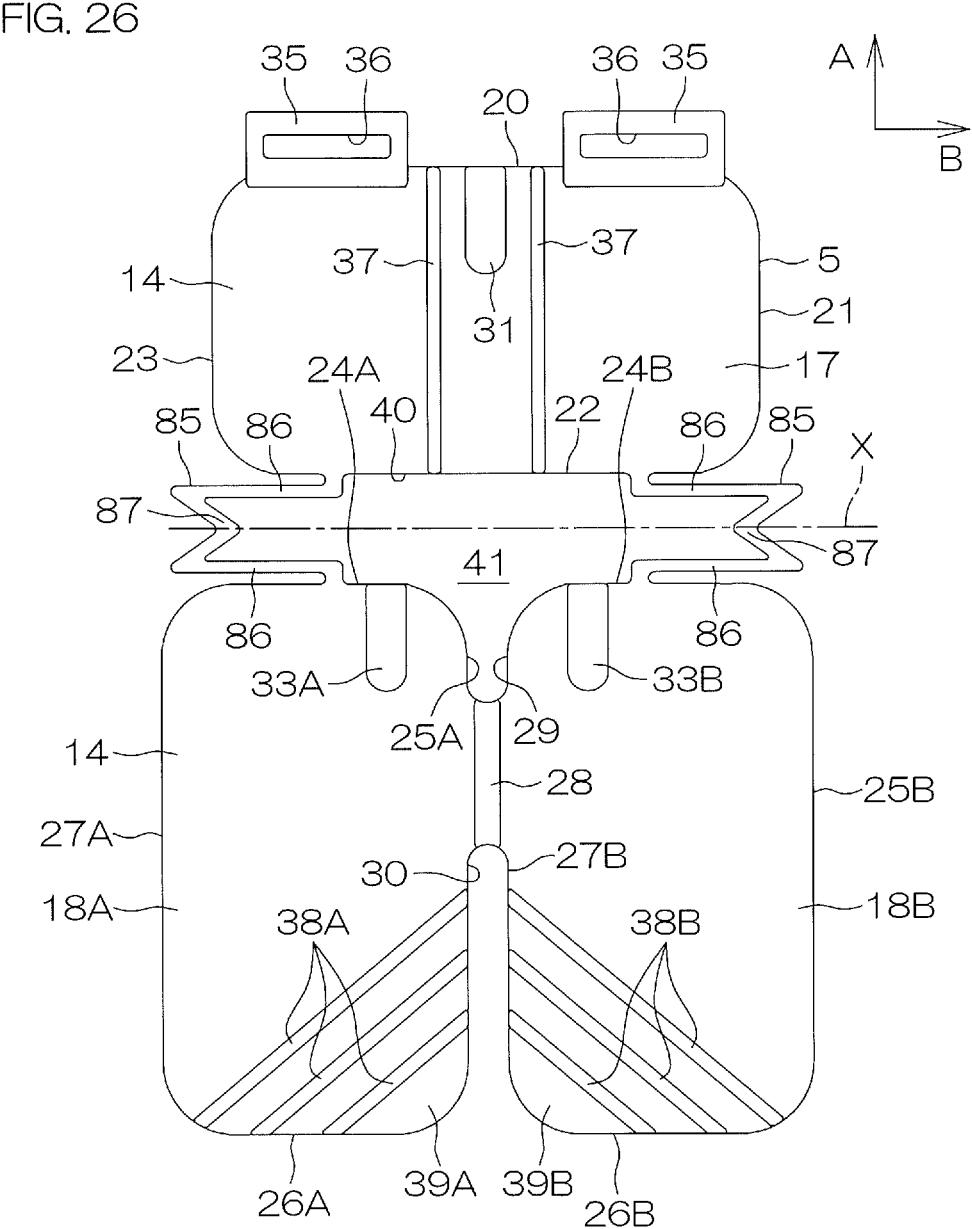
FIG. 26 is a front view showing a fourth modification example of the electrode for electrical stimulation therapy.
Figure 27:
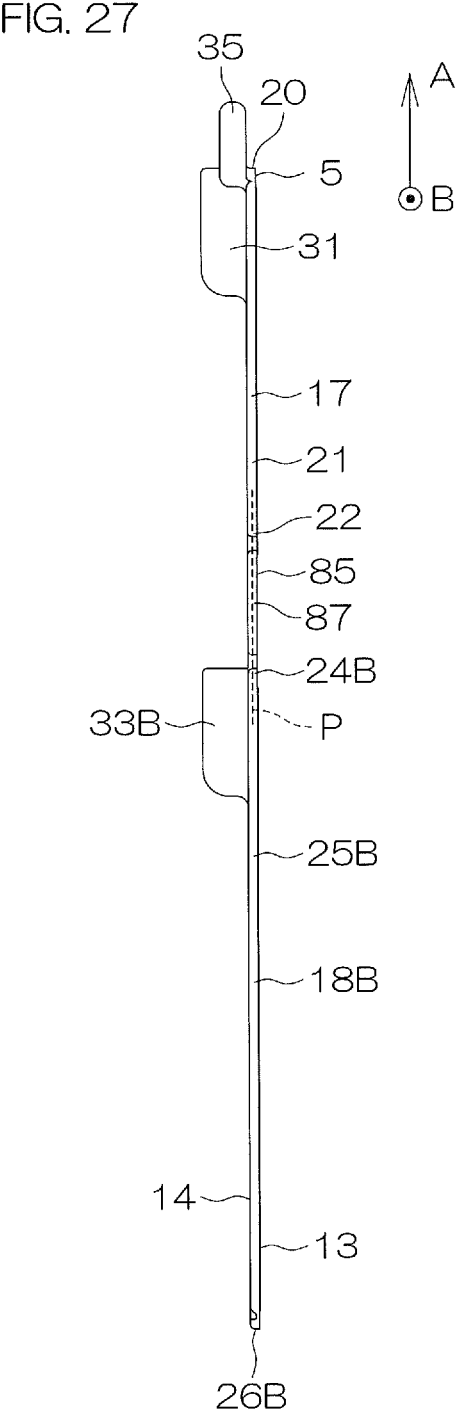
FIG. 27 is a right side view of the electrode for electrical stimulation therapy of FIG. 26.

FIG. 26 is a front view showing a fourth modification example of the electrode 2 for electrical stimulation therapy. FIG. 27 is a right side view of the electrode 2 for electrical stimulation therapy of FIG. 26.

The electrode 2 of the fourth modification example includes expandable/contractible portions 85 in place of the expandable/contractible portions 19 that are bulgingly curved to the second surface 14 side of the sheet body 5 in the sectional view in the direction A intersecting the virtual axial line X.

As shown in FIG. 26, the expandable/contractible portions 85 include one pair of expandable/contractible portions 85 that are mutually separated in the direction B along the virtual axial line X. One of the one pair of expandable/contractible portions 82 couples the third end portion 22 of the first region 17 and the first end portion 24A of the second region 18A and the other of the one pair of expandable/contractible portions 85 couples the third end portion 22 of the first region 17 and the first end portion 24B of the second region 18B. Each expandable/contractible portion 85 is of a folded line shape when the second surface 14 of the sheet body 5 is viewed from above.

More specifically, each expandable/contractible portion 85 includes one pair of first portions 86 extending along the direction B along the virtual axial line X and a second portion 87 extending along the direction A intersecting the virtual axial line X and coupling mutual one end portions of the one pair of first portions 86. Mutual other end portions of the one pair of first portions 86 are mutually separated in the direction A intersecting the virtual axial line X. In this fourth modification example, the expandable/contractible portions 85 are folded to an M shape in the region between the first region 17 and the second regions 18A and 18B.

Also, as shown in FIG. 27, the expandable/contractible portions 85 extend on a plane along the second surface 14 of the sheet body 5. Here, to extend on a plane along the second surface 14 means that, when the sheet body 5 is in the flat state, the expandable/contractible portions 85 do not protrude from either of the first surface 13 and the second surface 14 of the sheet body 5 and are disposed on the plane P parallel to the second surface 14 of the sheet body 5.

To manufacture the electrode 2 such as described above, for example, the reference electrode 6 and the one pair of stimulating electrodes 7A and 7B are first molded by compression molding. Next, the obtained reference electrode 6 and one pair of stimulating electrodes 7A and 7B are inserted as insert members in a mold and the material of the sheet body 5 (in this embodiment, silicone resin) is made to fill the mold interior. The electrode 2 can thereby be obtained as an insert molded article.

The electrode 2 of this fourth modification example includes the expandable/contractible portions 85 of M shapes. Therefore, when, as shown in FIG. 18, the human body 10 flexes (moves), each expandable/contractible portion 85 expands/contracts by the one pair of first portions 86 separating or approaching in accordance with the flexing. Application of an excessive force in a plane direction on the reference electrode 6 and the one pair of stimulating electrodes 7A and 7B can thereby be suppressed.

Also, end portions of the one pair of first portions 86 that are coupled by the second portion 87 are each positioned at an opposite side to the other expandable/contractible portion 85, that is, at the outer side. The shape of the sheet body 5 coupled by the expandable/contractible portions 85 can thereby be held with stability.

<Fifth Modification Example of Electrode 2>

Figure 28:
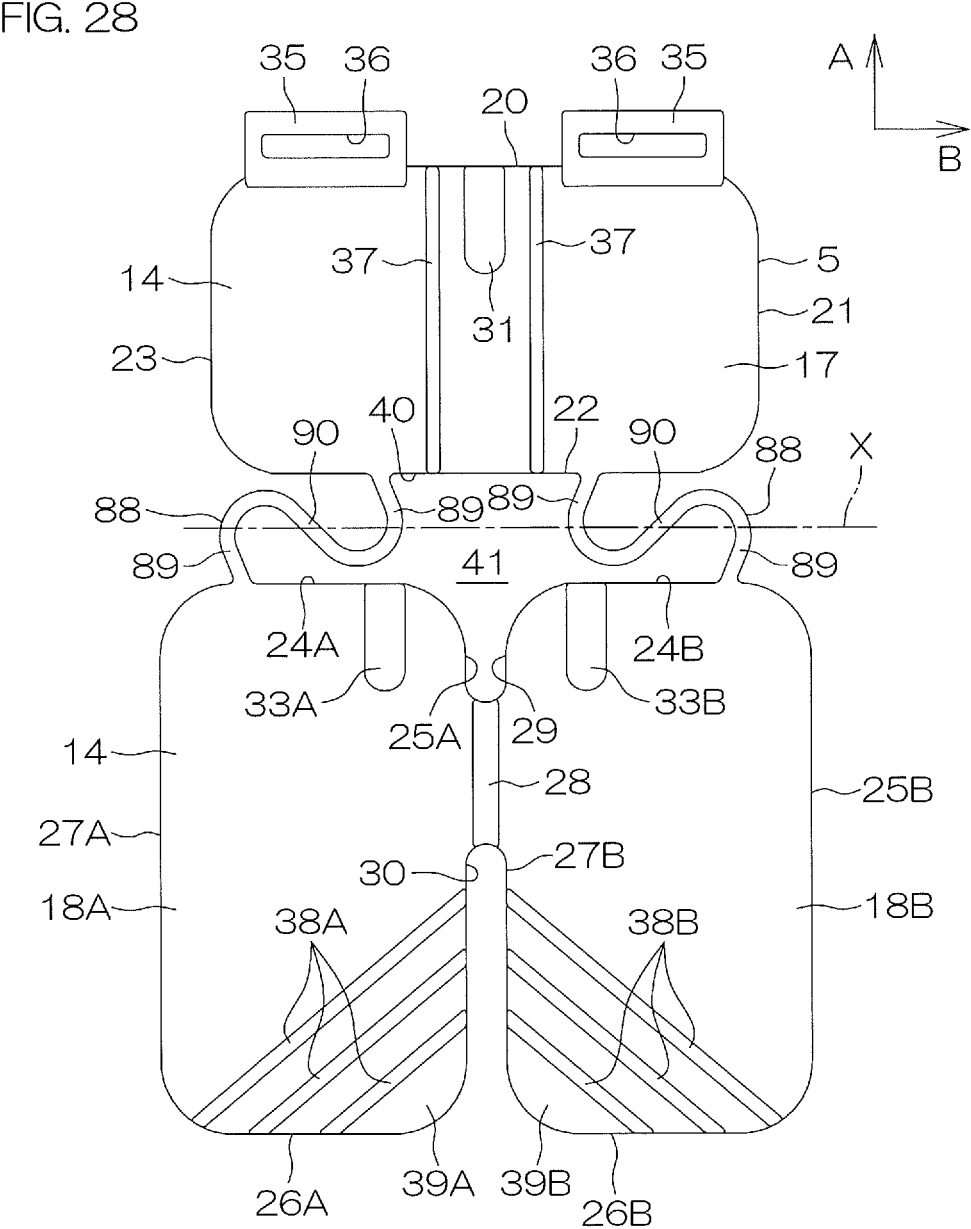
FIG. 28 is a front view showing a fifth modification example of the electrode for electrical stimulation therapy.
Figure 29:
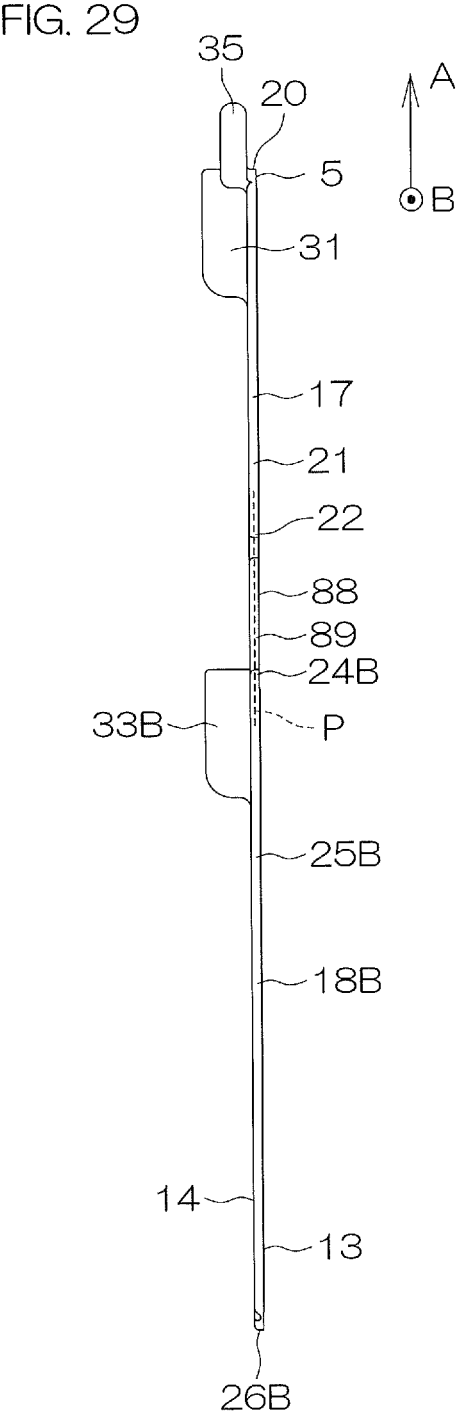
FIG. 29 is a right side view of the electrode for electrical stimulation therapy of FIG. 28.

FIG. 28 is a front view showing a fifth modification example of the electrode 2 for electrical stimulation therapy. FIG. 29 is a right side view of the electrode 2 for electrical stimulation therapy of FIG. 28.

The electrode 2 of the third modification example includes expandable/contractible portions 88 in place of the expandable/contractible portions 19 that are bulgingly curved to the second surface 14 side of the sheet body 5 in the sectional view in the direction A intersecting the virtual axial line X.

As shown in FIG. 28, the expandable/contractible portions 88 include one pair of expandable/contractible portions 88 that are mutually separated in the direction B along the virtual axial line X. One of the one pair of expandable/contractible portions 88 couples the third end portion 22 of the first region 17 and the first end portion 24A of the second region 18A and the other of the one pair of expandable/contractible portions 88 couples the third end portion 22 of the first region 17 and the first end portion 24B of the second region 18B. Each expandable/contractible portion 88 is of a folded line shape when the second surface 14 of the sheet body 5 is viewed from above.

More specifically, each expandable/contractible portion 88 includes one pair of first portions 89 extending along the direction A intersecting the virtual axial line X and a second portion 90 extending along the virtual axial line X and coupling mutual one end portions of the one pair of first portions 89. The one pair of first portions 89 are mutually separated in the direction B along the virtual axial line X. The second portion 90 couples an end portion at an opposite side to the first region 17 of the first portion 89 coupled to the first region 17 of the sheet body 5 and an end portion at an opposite side to the second region 18A or 18B of the first portion 89 coupled to the second region 18A or 18B of the sheet body 5. In this fifth modification example, the expandable/contractible portions 88 are folded to a sigmoidal shape in the region between the first region 17 and the second regions 18A and 18B.

Also, as shown in FIG. 29, the expandable/contractible portions 88 extend on a plane along the second surface 14 of the sheet body 5. Here, to extend on a plane along the second surface 14 means that, when the sheet body 5 is in the flat state, the expandable/contractible portions 88 do not protrude from either of the first surface 13 and the second surface 14 of the sheet body 5 and are disposed on the plane P parallel to the second surface 14 of the sheet body 5.

To manufacture the electrode 2 such as described above, for example, the reference electrode 6 and the one pair of stimulating electrodes 7A and 7B are first molded by compression molding. Next, the obtained reference electrode 6 and one pair of stimulating electrodes 7A and 7B are inserted as insert members in a mold and the material of the sheet body 5 (in this embodiment, silicone resin) is made to fill the mold interior. The electrode 2 can thereby be obtained as an insert molded article.

The electrode 2 of this fifth modification example includes the expandable/contractible portions 88 of sigmoidal shapes. Therefore, when, as shown in FIG. 18, the human body 10 flexes (moves), the expandable/contractible portions 88 expand/contract by the second portions 90 inclining along the direction A in accordance with the flexing. Application of an excessive force in a plane direction on the reference electrode 6 and the one pair of stimulating electrodes 7A and 7B can thereby be suppressed.

<Sixth Modification Example of Electrode 2>

Figure 30:
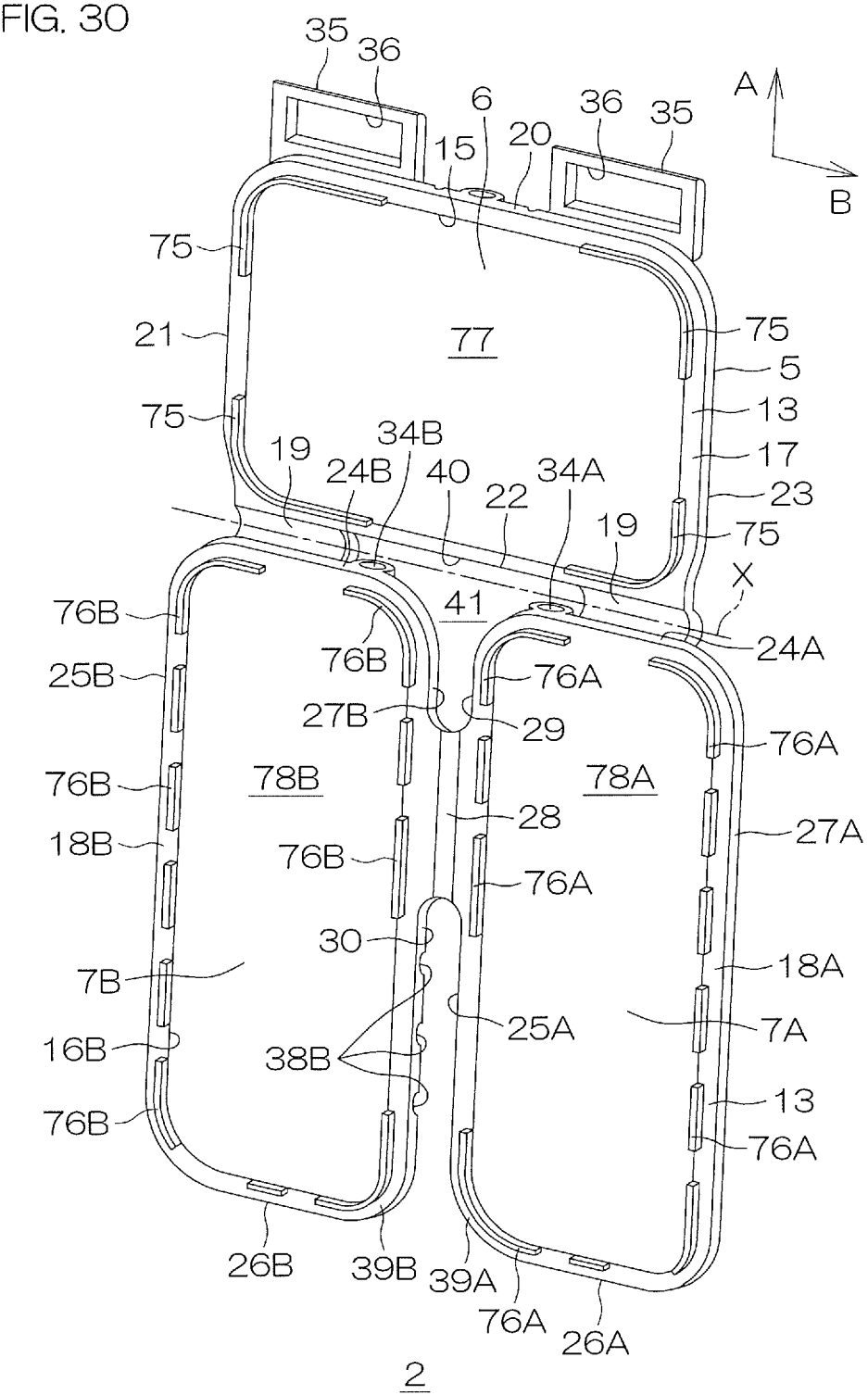
FIG. 30 is a perspective view showing a sixth modification example of the electrode for electrical stimulation therapy.

FIG. 30 is a perspective view showing a sixth modification example of the electrode 2 for electrical stimulation therapy.

Although, as described above, on the first surface 13 of the sheet body 5, peripheries of the reference electrode 6 and the one pair of stimulating electrodes 7A and 7B may be even, these may instead be protruded selectively. More specifically, protruding portions 75 may be formed at the periphery of the reference electrode 6 and protruding portions 76A and 76B may be respectively formed at peripheries of the one pair of stimulating electrodes 7A and 7B.

A protruding portion 75 may be formed at an appropriate location along an outer edge of the reference electrode 6 but preferably surrounds the reference electrode 6 and preferably, a plurality of protruding portions 75 are disposed to surround the reference electrode 6 at intervals from each other along the outer edge of the reference electrode 6 as shown in FIG. 30.

Here, to surround the reference electrode 6 means that the reference electrode 6 is disposed within a region 77 surrounded by a protruding portion 75 and if a plurality of protruding portions 75 are disposed as shown in FIG. 30, it suffices that the reference electrode 6 is disposed within the region 77 delimited inwardly by an entirety of the plurality of protruding portions 75. The region 77 surrounded by the protruding portions 75 is thereby formed on the reference electrode 6 and the conductive adhesive pad 8 can be disposed in the region 77.

A protruding portion 76A may be formed at an appropriate location along an outer edge of the stimulating electrode 7A but preferably surrounds the stimulating electrode 7A and preferably, a plurality of protruding portions 76A are disposed to surround the stimulating electrode 7A at intervals from each other along the outer edge of the stimulating electrode 7A as shown in FIG. 30.

Here, to surround the stimulating electrode 7A means that the stimulating electrode 7A is disposed within a region 78A surrounded by a protruding portion 76A and if a plurality of protruding portions 76A are disposed as shown in FIG. 30, it suffices that the stimulating electrode 7A is disposed within the region 78A delimited inwardly by an entirety of the plurality of protruding portions 76A. The region 78A surrounded by the protruding portions 76A is thereby formed on the stimulating electrode 7A and the conductive adhesive pad 9A can be disposed in the region 78A.

A protruding portion 76B may be formed at an appropriate location along an outer edge of the stimulating electrode 7B but preferably surrounds the stimulating electrode 7B and preferably, a plurality of protruding portions 76B are disposed to surround the stimulating electrode 7B at intervals from each other along the outer edge of the stimulating electrode 7B as shown in FIG. 30.

Here, to surround the stimulating electrode 7B means that the stimulating electrode 7B is disposed within a region 78B surrounded by a protruding portion 76B and if a plurality of protruding portions 76B are disposed as shown in FIG. 30, it suffices that the stimulating electrode 7B is disposed within the region 78B delimited inwardly by an entirety of the plurality of protruding portions 76B. The region 78B surrounded by the protruding portions 76B is thereby formed on the stimulating electrode 7B and the conductive adhesive pad 9B can be disposed in the region 78B.

As described above, according to the arrangement of FIG. 30, the protruding portions 75 and the protruding portions 76A and 76B are respectively formed at the peripheries of the reference electrode 6 and the one pair of stimulating electrodes 7A and 7B. Therefore, when the conductive adhesive pad 8 and the conductive adhesive pads 9A and 9B are respectively adhered to the region 77 and the regions 78A and 78B, the peripheries of the conductive adhesive pad 8 and the conductive adhesive pads 9A and 9B can be surrounded by the protruding portions 75 and the protruding portions 76A and 76B. Consequently, even when the electrode 2 is moved in a direction along a surface of the human body 10 during positioning of the electrode 2, the conductive adhesive pad 8 and the conductive adhesive pads 9A and 9B can be held by the protruding portions 75 and the protruding portions 76A and 76B and therefore, deviation of the conductive adhesive pad 8 and the conductive adhesive pads 9A and 9B can be suppressed.

Further, if the plurality of protruding portions 75 and the pluralities of protruding portions 76A and 76B are disposed at intervals from each other as shown in FIG. 30, the sheet body 5 bends easily at regions between mutually adjacent protruding portions 75 and between mutually adjacent protruding portions 76A and 76B and pliability of the sheet body 5 can also be secured.

Furthermore, the protruding portions 75 and the protruding portions 76A and 76B of the electrode 2 of this sixth modification example may be respectively formed at the periphery of the reference electrode 6 and the peripheries of the one pair of stimulating electrodes 7A and 7B of the electrode 2 of each of the first to fifth modification examples described above.

A description has been so far given of the embodiments of the present invention. However, the present invention can be carried out in other modes.

For example, the embodiment described above is of a mode where the reference electrode 6 and the one pair of stimulating electrodes 7A and 7B are opposed across the expandable/contractible portions 19. However, if the electrical stimulation therapeutic device 1 is not for the purpose of stimulating the sacral plexus that is positioned in bilateral symmetry in the human body 10 but is used for stimulating another portion of the human body 10, the one stimulating electrode 7A and the other stimulating electrode 7B may instead be opposed across the expandable/contractible portions 19.

Figure 31:
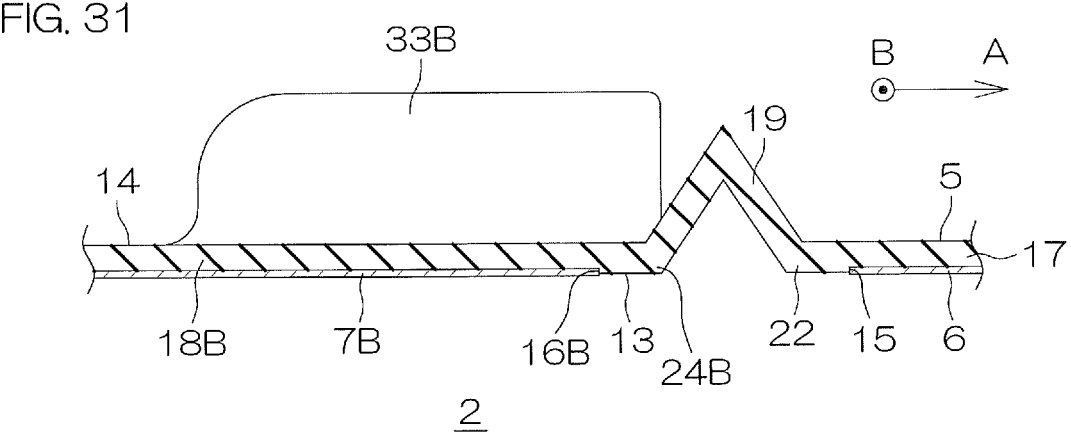
FIG. 31 is a diagram showing a modification example of an expandable/contractible portion.
Figure 32:
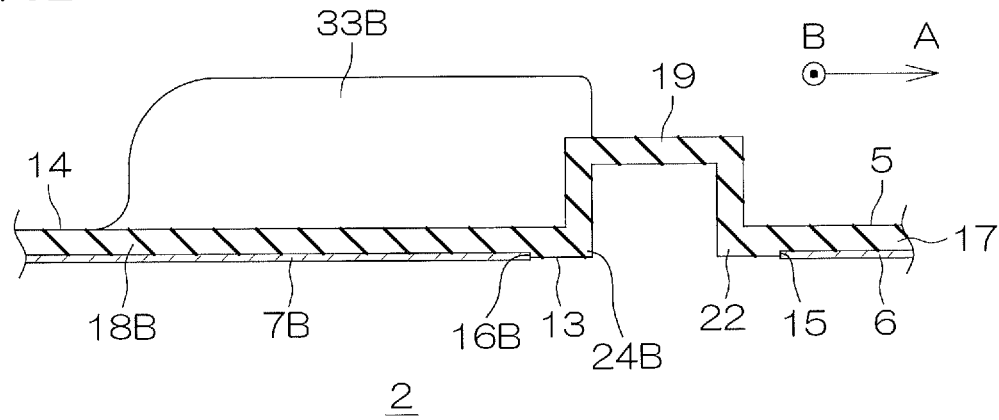
FIG. 32 is a diagram showing a modification example of an expandable/contractible portion.

For example, although with the electrode 2 shown in FIG. 1 to FIG. 18, the expandable/contractible portions 19 are of the arch shapes in the sectional view, as long as the expandable/contractible portions 19 are freely expandable/contractible, there is no restriction to this shape. For example, an expandable/contractible portion 19 may be of a triangular shape projecting toward the second surface 14 side in the sectional view as shown in FIG. 31 or may be of a quadrilateral shape having a surface parallel to the second surface 14 in the sectional view as shown in FIG. 32.

Figure 33:
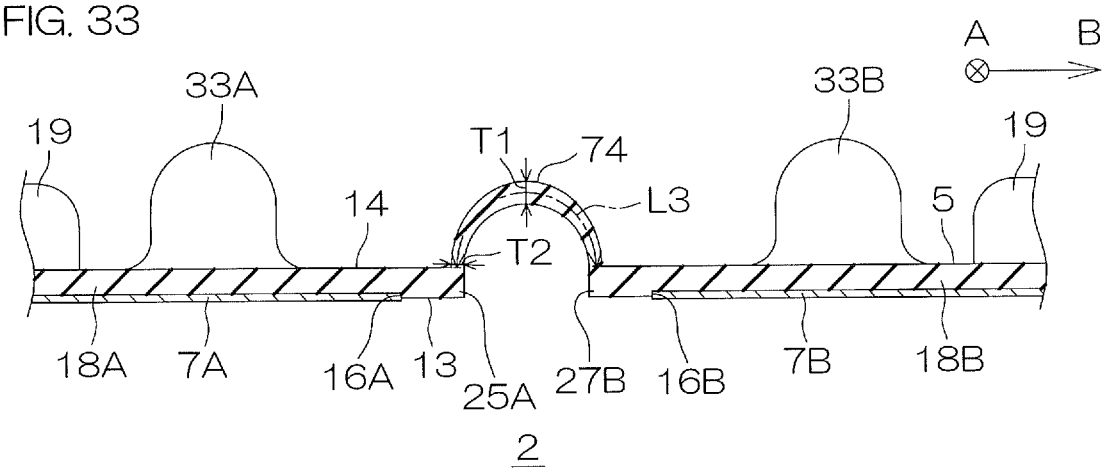
FIG. 33 is a diagram showing a modification example of a second expandable/contractible portion of FIG. 19.

For example, although the second expandable/contractible portion 74 in the electrode 2 of FIG. 19 has a uniform thickness along a periphery of the arch shape, a thickness T1 of an apex portion of the arch may be thicker than a thickness T2 at base portions of the arch (in vicinities of connecting portions to the second regions 18A and 18B) as shown in FIG. 33. In this case, for example, the thickness T1 may be approximately 2.0 mm and the thickness T2 may be approximately 0.3 mm.

For example, although with the embodiment described above, the conductive adhesive pads 8, 9A, and 9B are used as members for transmitting the current output from the one pair of stimulating electrodes 7A and 7B, other conductive members may be used in place of the conductive adhesive pads 8, 9A, and 9B. For example, if the electrode 2 can be fixed to the human body 10 with a belt or tape, etc., conductive members without an adhesive property may be interposed between the reference electrode 6 and the one pair of stimulating electrodes 7A and 7B and the human body 10.

For example, although with the embodiment described above, the arrangement of the electrode 2 used in the electrical stimulation therapeutic device 1 of a portable type was described, the electrode 2 may also be applied to an electrical stimulation therapeutic device of a table top (stationary type). Such a table top electrical stimulation therapeutic device is used in common by a plurality of patients in a medical institution.

For example, although with the embodiment described above, the urination disorder treatment device (fecal incontinence treatment device) was taken up as an example of the electrical stimulation therapeutic device, the present invention is not restricted to a urination disorder treatment device or a fecal incontinence treatment device and can be applied generally to devices used for an electrical stimulation therapeutic method intended for other disorders besides these.

In addition, the design of the present invention may be modified in various ways without departing from the scope described in the claims.

The present application corresponds to Japanese Patent Application No. 2019-042976 filed on Mar. 8, 2019 in the Japan Patent Office, and the entire disclosure of this application is incorporated herein by reference.

REFERENCE SIGNS LIST

1: Electrical stimulation therapeutic device
2: Electrode
3: Device body
4: Wiring cord
5: Sheet body
6: Reference electrode
7A, 7B: Stimulating electrode
8: Conductive adhesive pad
9A, 9B: Conductive adhesive pad
10: Human body
11: Operation button
12: Touch panel
13: First surface
14: Second surface
15: Recess
16A, 16B: Recess
17: First region
18A, 18B: Second region
19: Expandable/contractible portion
20: First end portion
21: Second end portion
22: Third end portion
23: Fourth end portion
24A, 24B: First end portion
25A, 25B: Second end portion
26A, 26B: Third end portion
27A, 27B: Fourth end portion
28: Thin portion
29: Slit
30: Slit
31: First terminal
32: First socket
33A, 33B: Second terminal
34A, 34B: Second socket
35: Assistive device attaching portion
36: Slit
37: Thin portion
38A, 38B: Thin portion
39A, 39B: Corner portion
40: Slit
41: Opening
42: Casing
43: Start/stop button
44: First socket
45: Second socket
46: Composite wiring
47: Power supply side plug terminal
48: First plug terminal
49A, 49B: Second plug terminal
50: First wiring
51A, 51B: Second wiring
52: Power supply side terminal body
53: Power supply side plug
54: Connecting portion
55: Upper surface portion
56: Lower surface portion
57: Side surface portion
58: Front surface portion
59: Dummy wiring
60: First terminal body
61: First plug
62: Connecting portion
63: Upper surface portion
64: Lower surface portion
65: Side surface portion
66: Front surface portion
67: Wiring space
68: Connecting portion
69A, 69B: Second terminal body
70A, 70B: Second plug
71A, 71B: Iliac crest
72: Thumb
73: Sacrum
74: Second expandable/contractible portion
75: Protruding portion
76A, 76B: Protruding portion
77: Region
78A, 78B: Region
79: Expandable/contractible portion
80: One surface
81: Other surface
82: Expandable/contractible portion
83: First portion
84: Second portion
85: Expandable/contractible portion
86: First portion
87: Second portion
88: Expandable/contractible portion
89: First portion
90: Second portion
X: Virtual axial line

The invention claimed is:

1. An electrode for electrical stimulation therapy comprising: a sheet body of flat shape that has a first surface facing a skin of a human body and a second surface at an opposite side to the first surface; and
at least one pair of flat electrodes that are provided at the first surface side of the sheet body and are mutually separated;
wherein the sheet body includes an expandable/contractible portion that is formed on a virtual axial line extending between the one pair of flat electrodes and is freely expandable/contractible in a direction intersecting the virtual axial line, and the expandable/contractible portion includes an expandable/contractible portion that is formed along the virtual axial line and is bulgingly curved to the second surface side of the sheet body in a sectional view in the direction intersecting the virtual axial line.

2. The electrode for electrical stimulation therapy according to claim 1, wherein the expandable/contractible portion is bulged in an arch shape to the second surface side of the sheet body in the sectional view when the sheet body is in a flat state.

3. The electrode for electrical stimulation therapy according to claim 2, wherein the expandable/contractible portion of the arch shape has a perimeter of 1 cm to 3 cm in the sectional view.

4. An electrode for electrical stimulation therapy comprising:
a sheet body of flat shape that has a first surface facing a skin of a human body and a second surface at an opposite side to the first surface; and
at least one pair of flat electrodes that are provided at the first surface side of the sheet body and are mutually separated;
wherein
the sheet body includes an expandable/contractible portion that is formed on a virtual axial line extending between the one pair of flat electrodes and is freely expandable/contractible in a direction intersecting the virtual axial line,
the sheet body includes a first region at one side and a second region at another side that are opposed across the expandable/contractible portion in the direction intersecting the virtual axial line,
the at least one pair of flat electrodes include a first electrode disposed in the first region and a second electrode disposed in the second region, and
the first electrode includes one reference electrode and the second electrode includes one pair of stimulating electrodes.

5. An electrode for electrical stimulation therapy comprising:
a sheet body of flat shape that has a first surface facing a skin of a human body and a second surface at an opposite side to the first surface; and
at least one pair of flat electrodes that are provided at the first surface side of the sheet body and are mutually separated;
wherein
the sheet body includes an expandable/contractible portion that is formed on a virtual axial line extending between the one pair of flat electrodes and is freely expandable/contractible in a direction intersecting the virtual axial line,
the sheet body includes a first region at one side and a second region at another side that are opposed across the expandable/contractible portion in the direction intersecting the virtual axial line,
the at least one pair of flat electrodes include a first electrode disposed in the first region and a second electrode disposed in the second region,
the expandable/contractible portion includes one pair of expandable/contractible portions that are mutually separated in a direction along the virtual axial line, and
an opening demarcated by the first region, the second region, and the one pair of expandable/contractible portions is formed in the sheet body.

6. An electrode for electrical stimulation therapy comprising:
a sheet body of flat shape that has a first surface facing a skin of a human body and a second surface at an opposite side to the first surface;
at least one pair of flat electrodes that are provided at the first surface side of the sheet body and are mutually separated; and
a protruding portion formed in a periphery of at least one of the one pair of flat electrodes within the first surface of the sheet body,
wherein the sheet body includes an expandable/contractible portion that is formed on a virtual axial line extending between the one pair of flat electrodes and is freely expandable/contractible in a direction intersecting the virtual axial line.

7. The electrode for electrical stimulation therapy according to claim 6, wherein a plurality of the protruding portions are disposed at intervals from each other such as to surround the flat electrode.

8. An electrical stimulation therapeutic device comprising:
a device body; and
the electrode for electrical stimulation therapy according to claim 1 that is electrically connected to the device body.

9. An electrical stimulation therapeutic device comprising:
a device body;
the electrode for electrical stimulation therapy according to claim 4; and
a wiring member that connects the device body and the electrode for electrical stimulation therapy;
wherein
the electrode for electrical stimulation therapy includes
a first terminal that is provided at the second surface side of the first region of the sheet body, has a first socket, and is conductive to the reference electrode, and
one pair of second terminals that are provided at the second surface side of the second region of the sheet body, have second sockets facing the same direction as the first socket, and are conductive to the one pair of stimulating electrodes, and
the wiring member includes:
a composite wiring that incorporates at least a first wiring and one pair of second wirings,
a first plug terminal that includes a terminal body provided at one end side of the composite wiring and having an opposing surface opposing the first socket and a first plug protruding from the opposing surface of the terminal body, is conductive to the first wiring, and is inserted into the first socket, and
one pair of second plug terminals that are conductive to the one pair of second wirings and include second plugs to be inserted into the second sockets,
the one pair of second wirings pass through an interior of the terminal body and extend from the opposing surface of the terminal body, and
the one pair of second plug terminals are provided at tip portions of the one pair of second wirings.

10. The electrical stimulation therapeutic device according to claim 9, wherein
the one pair of second wirings include one pair of connecting portions to the opposing surface of the terminal body and
the one pair of connecting portions are disposed to sandwich the first plug.

11. The electrical stimulation therapeutic device according to claim 8 that includes a urination disorder treatment device.

\* \* \* \* \*